(12) United States Patent
Mernoe

(10) Patent No.: US 7,753,879 B2
(45) Date of Patent: Jul. 13, 2010

(54) DISPOSABLE MEDICINE DISPENSING DEVICE

(75) Inventor: Morten Mernoe, Charlottenlund (DK)

(73) Assignee: M2 Group Holdings, Inc., Sunnyvale, CA (US)

( * ) Notice: Subject to any disclaimer, the term of this patent is extended or adjusted under 35 U.S.C. 154(b) by 548 days.

(21) Appl. No.: 10/587,911

(22) PCT Filed: Jan. 28, 2005

(86) PCT No.: PCT/DK2005/000060

§ 371 (c)(1), (2), (4) Date: Apr. 20, 2007

(87) PCT Pub. No.: WO2005/072794

PCT Pub. Date: Aug. 11, 2005

(65) Prior Publication Data

US 2007/0276329 A1 Nov. 29, 2007

(30) Foreign Application Priority Data

Jan. 29, 2004 (DK) ............................... 2004 00123
Mar. 17, 2004 (DK) ............................... 2004 00428

(51) Int. Cl.
*A61M 37/00* (2006.01)

(52) U.S. Cl. .................. 604/131; 604/145; 604/155; 604/218; 604/223; 604/228; 604/232; 604/235

(58) Field of Classification Search ................ 604/145, 604/155, 218, 223, 228, 232, 235, 131
See application file for complete search history.

(56) References Cited

U.S. PATENT DOCUMENTS 2,605,765 A 8/1952 Kollsman (Continued)

FOREIGN PATENT DOCUMENTS

DE 196 27 619 1/1998

(Continued)

OTHER PUBLICATIONS

U.S. Appl. No. 11/362,616.

(Continued)

*Primary Examiner*—Nicholas D Lucchesi
*Assistant Examiner*—Scott Medway
(74) *Attorney, Agent, or Firm*—Fish & Richardson P.C.

(57) ABSTRACT

A combination of a disposable, wearable, self-contained medicine dispensing device, a cylindrical medicine container 52 incorporating a piston and having an open distal end and a proximal end closed by a closure body 54 made of a material, preferably silicone, that can be perforated by a needle, and a catheter device 16 having adhesive means 26 for attaching the catheter device to the skin of a user of the combination, the dispensing device comprising a housing 34, 36 having a compartment for receiving the container and further a not shown piston rod for displacing the piston towards the closed proximal end and actuating means for displacing the piston rod, the catheter device comprising a sealing ring 56'for receiving the closure body, and the dispensing device and the catheter device comprising co-operating attachment means for attaching the dispensing device to the catheter device with the container received in the compartment with the piston rod abutting the piston and the closure body received in the sealing ring.

20 Claims, 24 Drawing Sheets

U.S. PATENT DOCUMENTS

| | | | |
|---|---|---|---|
| 3,886,938 A | 6/1975 | Szabo et al. | |
| 4,077,405 A | 3/1978 | Haerten et al. | |
| 4,231,368 A | 11/1980 | Becker | |
| 4,265,241 A | 5/1981 | Portner et al. | |
| 4,300,554 A | 11/1981 | Hessberg et al. | |
| 4,313,439 A | 2/1982 | Babb et al. | |
| 4,398,908 A | 8/1983 | Siposs | |
| 4,435,173 A | 3/1984 | Siposs et al. | |
| 4,443,218 A | 4/1984 | DeCant, Jr. et al. | |
| 4,493,704 A | 1/1985 | Beard et al. | |
| 4,529,401 A | 7/1985 | Leslie et al. | |
| 4,850,817 A | 7/1989 | Nason et al. | |
| 5,045,064 A | 9/1991 | Idriss | |
| 5,088,981 A | 2/1992 | Howson et al. | |
| 5,190,522 A | 3/1993 | Wojcicki et al. | |
| 5,250,027 A | 10/1993 | Lewis et al. | |
| 5,261,882 A | 11/1993 | Sealfon et al. | |
| 5,314,412 A | 5/1994 | Rex | |
| 5,335,994 A | 8/1994 | Girones | |
| 5,338,157 A | 8/1994 | Blomquist | |
| 5,342,180 A | 8/1994 | Daoud | |
| 5,395,340 A | 3/1995 | Lee | |
| 5,411,487 A | 5/1995 | Castagna | |
| 5,545,143 A | 8/1996 | Fischell et al. | |
| 5,551,850 A | 9/1996 | Williamson et al. | |
| 5,569,186 A | 10/1996 | Lord et al. | |
| 5,626,566 A | 5/1997 | Petersen et al. | |
| 5,637,095 A | 6/1997 | Nason et al. | |
| 5,665,065 A | 9/1997 | Colman et al. | |
| 5,741,216 A | 4/1998 | Hemmingsen et al. | |
| 5,772,635 A | 6/1998 | Dastur et al. | |
| 5,816,306 A | 10/1998 | Giacomel | |
| 5,852,803 A | 12/1998 | Ashby, III et al. | |
| 5,919,167 A * | 7/1999 | Mulhauser et al. | 604/131 |
| 5,925,018 A | 7/1999 | Ungerstedt | |
| 5,928,201 A | 7/1999 | Poulsen et al. | |
| 5,947,934 A | 9/1999 | Hansen et al. | |
| 5,951,530 A | 9/1999 | Steengaard et al. | |
| 5,957,889 A | 9/1999 | Poulsen et al. | |
| 5,984,894 A | 11/1999 | Poulsen et al. | |
| 5,984,897 A | 11/1999 | Petersen et al. | |
| 5,997,475 A | 12/1999 | Bortz | |
| 6,003,736 A | 12/1999 | Ljunggren | |
| 6,010,485 A | 1/2000 | Buch-Rasmussen et al. | |
| 6,033,377 A | 3/2000 | Rasmussen et al. | |
| 6,045,537 A | 4/2000 | Klitmose | |
| 6,074,372 A | 6/2000 | Hansen | |
| 6,110,149 A | 8/2000 | Klitgaard et al. | |
| 6,156,014 A | 12/2000 | Petersen et al. | |
| 6,171,276 B1 | 1/2001 | Lippe et al. | |
| 6,231,540 B1 | 5/2001 | Smedegaard | |
| 6,248,067 B1 | 6/2001 | Causey, III et al. | |
| 6,248,090 B1 | 6/2001 | Jensen et al. | |
| 6,248,093 B1 | 6/2001 | Moberg | |
| 6,277,098 B1 | 8/2001 | Klitmose et al. | |
| 6,302,855 B1 | 10/2001 | Lav et al. | |
| 6,302,869 B1 * | 10/2001 | Klitgaard | 604/218 |
| 6,375,638 B2 | 4/2002 | Nason et al. | |
| 6,379,339 B1 | 4/2002 | Klitgaard et al. | |
| 6,381,496 B1 | 4/2002 | Meadows et al. | |
| 6,404,098 B1 | 6/2002 | Kayama et al. | |
| 6,427,088 B1 | 7/2002 | Bowman, IV et al. | |
| 6,461,331 B1 | 10/2002 | Van Antwerp | |
| 6,474,219 B2 | 11/2002 | Klitmose et al. | |
| 6,485,461 B1 | 11/2002 | Mason et al. | |
| 6,508,788 B2 | 1/2003 | Preuthun | |
| 6,524,280 B2 | 2/2003 | Hansen et al. | |
| 6,533,183 B2 | 3/2003 | Aasmul et al. | |
| 6,537,251 B2 | 3/2003 | Klitmose | |
| 6,540,672 B1 | 4/2003 | Simonsen et al. | |
| 6,544,229 B1 | 4/2003 | Danby et al. | |
| 6,547,764 B2 | 4/2003 | Larsen et al. | |
| 6,551,276 B1 | 4/2003 | Mann et al. | |
| 6,554,798 B1 | 4/2003 | Mann et al. | |
| 6,554,800 B1 | 4/2003 | Nezhadian et al. | |
| 6,558,320 B1 | 5/2003 | Causey, III et al. | |
| 6,558,351 B1 | 5/2003 | Steil et al. | |
| 6,562,001 B2 | 5/2003 | Lebel et al. | |
| 6,562,011 B1 | 5/2003 | Buch-Rasmussen et al. | |
| 6,564,105 B2 | 5/2003 | Starkweather et al. | |
| 6,569,126 B1 | 5/2003 | Poulsen et al. | |
| 6,571,128 B2 | 5/2003 | Lebel et al. | |
| 6,577,899 B2 | 6/2003 | Lebel et al. | |
| 6,582,404 B1 | 6/2003 | Klitgaard et al. | |
| 6,585,644 B2 | 7/2003 | Lebel et al. | |
| 6,585,699 B2 | 7/2003 | Ljunggreen et al. | |
| 6,605,067 B1 | 8/2003 | Larsen | |
| 6,613,019 B2 | 9/2003 | Munk | |
| 6,641,533 B2 | 11/2003 | Causey, III et al. | |
| 6,648,821 B2 | 11/2003 | Lebel et al. | |
| 6,650,951 B1 | 11/2003 | Jones et al. | |
| 6,656,158 B2 | 12/2003 | Mahoney et al. | |
| 6,656,159 B2 * | 12/2003 | Flaherty | 604/131 |
| 6,659,948 B2 | 12/2003 | Lebel et al. | |
| 6,659,978 B1 | 12/2003 | Kasuga et al. | |
| 6,659,980 B2 | 12/2003 | Moberg et al. | |
| 6,663,602 B2 | 12/2003 | Møller | |
| 6,668,196 B1 | 12/2003 | Villegas et al. | |
| 6,669,669 B2 | 12/2003 | Flaherty et al. | |
| 6,687,546 B2 | 2/2004 | Lebel et al. | |
| 6,691,043 B2 | 2/2004 | Ribeiro, Jr. | |
| 6,692,457 B2 | 2/2004 | Flaherty | |
| 6,692,472 B2 | 2/2004 | Hansen et al. | |
| 6,694,191 B2 | 2/2004 | Starkweather et al. | |
| 6,699,218 B2 | 3/2004 | Flaherty et al. | |
| 6,702,779 B2 | 3/2004 | Connelly et al. | |
| 6,715,516 B2 | 4/2004 | Ohms et al. | |
| 6,716,198 B2 | 4/2004 | Larsen | |
| 6,723,072 B2 | 4/2004 | Flaherty et al. | |
| 6,733,446 B2 | 5/2004 | Lebel et al. | |
| 6,736,796 B2 | 5/2004 | Shekalim | |
| 6,740,059 B2 | 5/2004 | Flaherty | |
| 6,740,072 B2 | 5/2004 | Starkweather et al. | |
| 6,740,075 B2 | 5/2004 | Lebel et al. | |
| 6,744,350 B2 | 6/2004 | Blomquist | |
| 6,749,587 B2 | 6/2004 | Flaherty | |
| 6,752,787 B1 | 6/2004 | Causey, III et al. | |
| 6,758,810 B2 | 7/2004 | Lebel et al. | |
| 6,768,425 B2 | 7/2004 | Flaherty et al. | |
| 6,780,156 B2 | 8/2004 | Haueter et al. | |
| 6,786,246 B2 | 9/2004 | Ohms et al. | |
| 6,786,890 B2 | 9/2004 | Preuthun et al. | |
| 6,796,970 B1 | 9/2004 | Klitmose et al. | |
| 6,799,149 B2 | 9/2004 | Hartlaub | |
| 6,809,653 B1 | 10/2004 | Mann et al. | |
| 6,810,290 B2 | 10/2004 | Lebel et al. | |
| 6,811,533 B2 | 11/2004 | Lebel et al. | |
| 6,811,534 B2 | 11/2004 | Bowman, IV et al. | |
| 6,813,519 B2 | 11/2004 | Lebel et al. | |
| 6,827,702 B2 | 12/2004 | Lebel et al. | |
| 6,830,558 B2 | 12/2004 | Flaherty et al. | |
| 6,852,104 B2 | 2/2005 | Blomquist | |
| 6,854,620 B2 | 2/2005 | Ramey | |
| 6,854,653 B2 | 2/2005 | Eilersen | |
| 6,855,129 B2 | 2/2005 | Jensen et al. | |
| 6,872,200 B2 | 3/2005 | Mann et al. | |
| 6,873,268 B2 | 3/2005 | Lebel et al. | |
| 6,878,132 B2 | 4/2005 | Kipfer | |
| 6,893,415 B2 | 5/2005 | Madsen et al. | |
| 6,899,695 B2 | 5/2005 | Herrera | |
| 6,899,699 B2 | 5/2005 | Enggaard | |
| 6,922,590 B2 | 7/2005 | Whitehurst | |
| 6,936,006 B2 | 8/2005 | Sabra | |
| 6,936,029 B2 | 8/2005 | Mann et al. | |

| | | |
|---|---|---|
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,144,384 B2 * | 12/2006 | Gorman et al. ............. 604/131 |
| 7,232,423 B2 | 6/2007 | Mernoe |
| 2001/0056262 A1 | 12/2001 | Cabiri |
| 2002/0004651 A1 | 1/2002 | Ljunggreen et al. |
| 2002/0007154 A1 | 1/2002 | Hansen et al. |
| 2002/0040208 A1 | 4/2002 | Flaherty et al. |
| 2002/0077598 A1 * | 6/2002 | Yap et al. .................... 604/155 |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0199824 A1 * | 10/2003 | Mahoney et al. ............ 604/155 |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245878 A1 | 11/2005 | Mernoe |
| 2005/0251097 A1 | 11/2005 | Mernoe |
| 2005/0267402 A1 | 12/2005 | Stewart et al. |
| 2005/0273059 A1 | 12/2005 | Mernoe |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073236 A1 | 3/2007 | Mernoe et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |

FOREIGN PATENT DOCUMENTS

| | | |
|---|---|---|
| DE | 102 36 669 | 2/2004 |
| EP | 0 580 723 | 10/1995 |
| EP | 0 612 004 | 3/1997 |
| EP | 0 496 141 | 4/1997 |
| EP | 1 045 146 | 10/2000 |
| EP | 1 136 698 | 9/2001 |
| EP | 0 721 358 | 5/2002 |
| EP | 1 177 802 | 9/2004 |
| EP | 1 495 775 | 1/2005 |
| EP | 1 527 792 | 5/2005 |
| FR | 2 585 252 | 1/1987 |
| GB | 747 701 | 4/1956 |
| GB | 2 218 831 | 11/1989 |
| JP | 11-010036 | 1/1999 |
| WO | WO 90/15928 | 12/1990 |
| WO | WO 97/21457 | 6/1997 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO 02/100469 | 12/2002 |
| WO | WO 03/103763 | 12/2003 |
| WO | WO 2004/056412 | 7/2004 |
| WO | WO 2004/110526 | 12/2004 |
| WO | WO 2005/039673 | 5/2005 |
| WO | WO 2005/072794 | 8/2005 |
| WO | WO 2005/072795 | 8/2005 |
| WO | WO 2006/105792 | 10/2006 |
| WO | WO 2006/105793 | 10/2006 |
| WO | WO 2006/105794 | 10/2006 |

OTHER PUBLICATIONS

Medtronic News Release, "Medtronic Receives FDA Approval for World's First Insulin Pump with Real-time Continuous Glucose Monitoring," Apr. 13, 2006, 3 pages.

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

Collins and Lee, "Microfluidic flow transducer based on the measurement of electrical admittance," *Lab Chip*, 2004, 4:7-10.

* cited by examiner

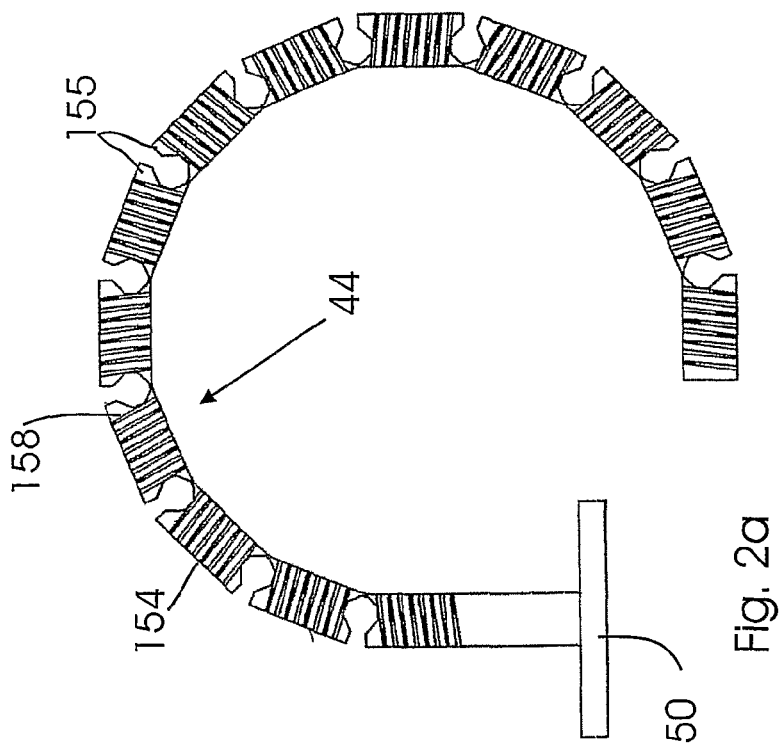
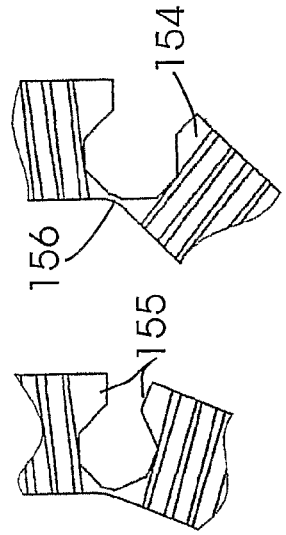
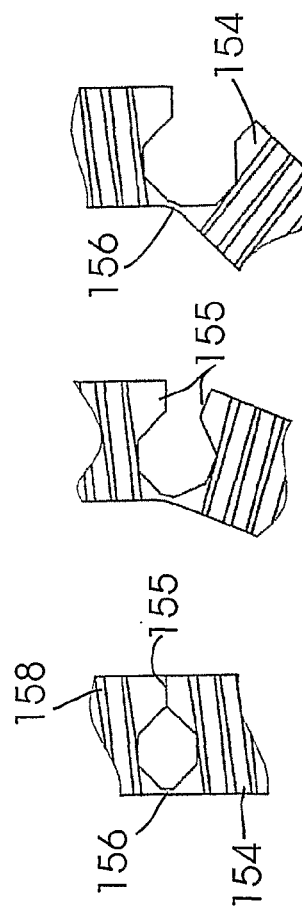
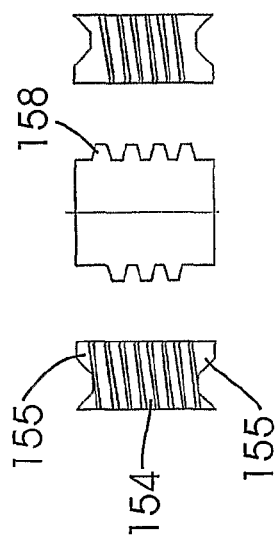
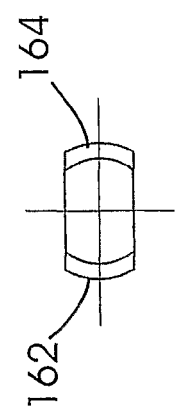

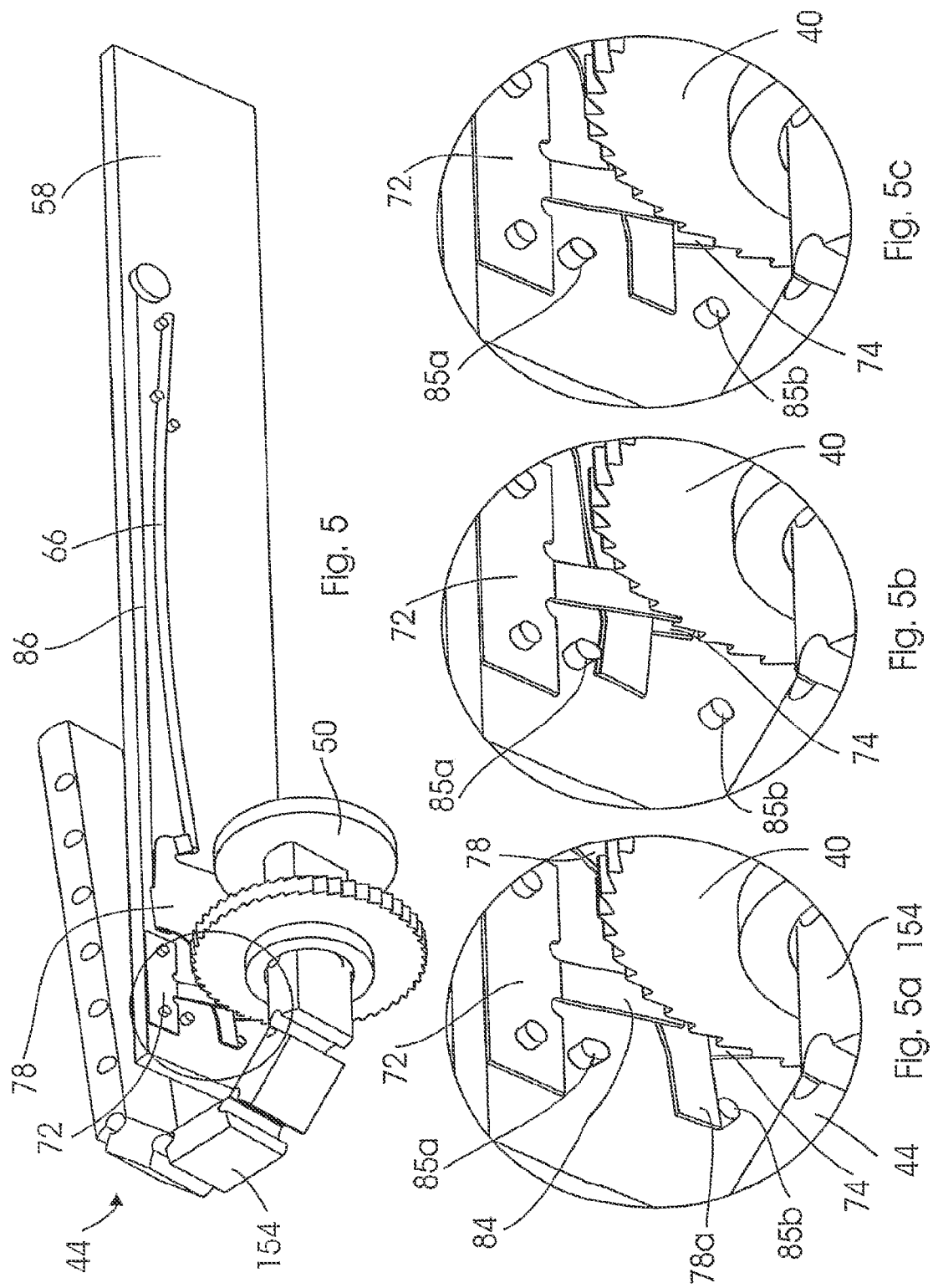

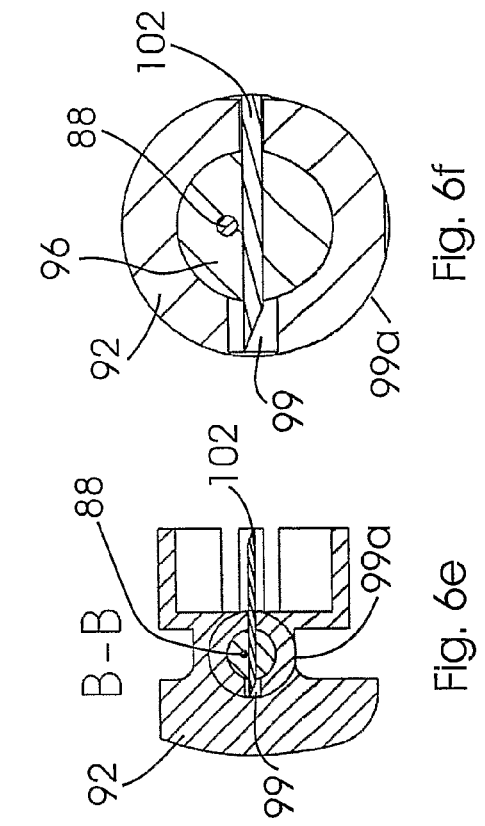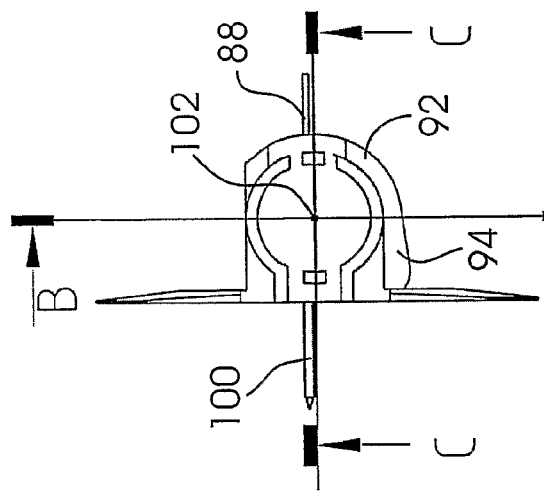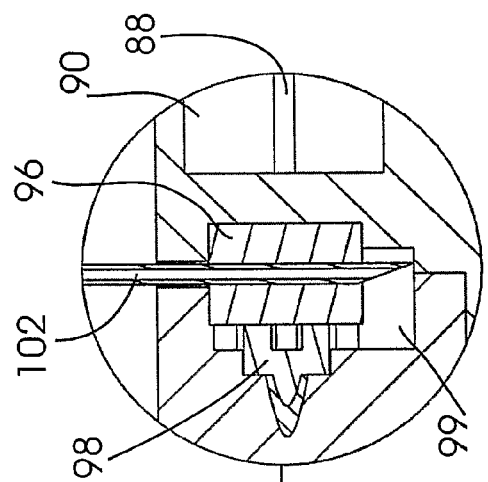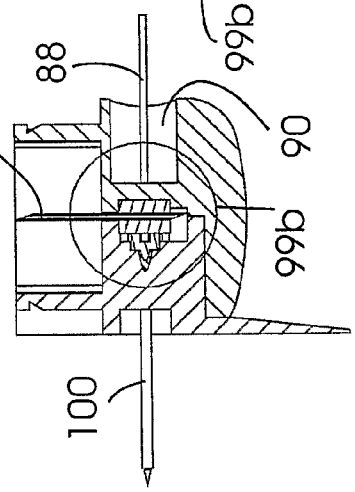

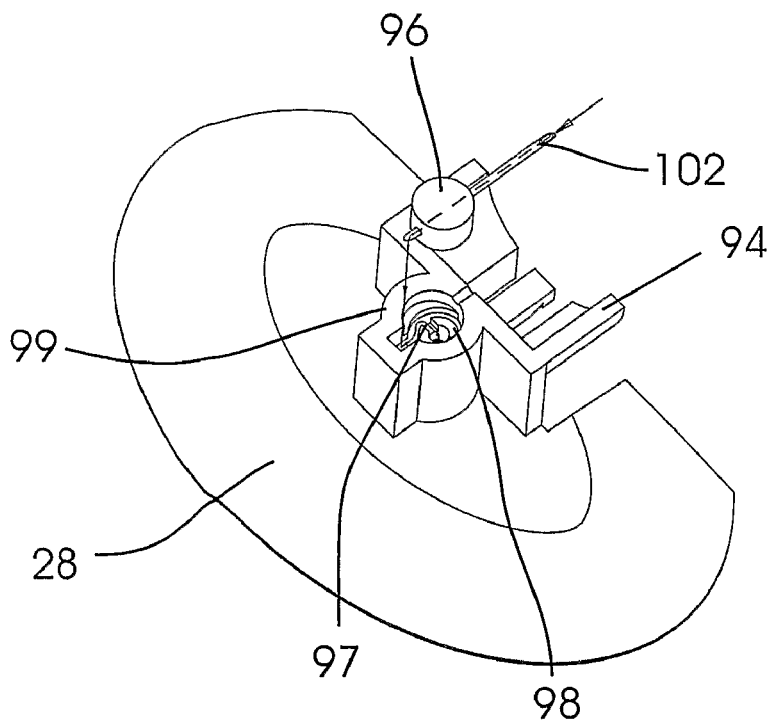
Fig. 6i
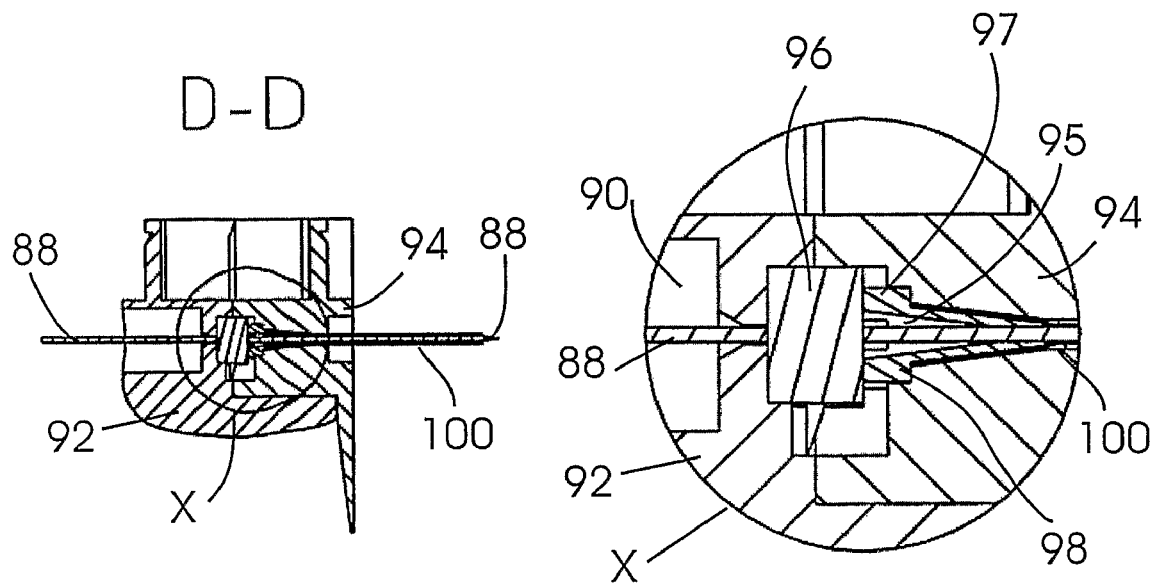
Fig. 6j
Fig. 6k

DISPOSABLE MEDICINE DISPENSING DEVICE

This application is a national stage application under 35 U.S.C. §371 that claims the benefit of PCT/DK2005/000060 filed on Jan. 28, 2005 and entitled DISPOSABLE MEDICINE DISPENSING DEVICE, which claims priority to the following Denmark patent applications: serial no. PA 2004 00123 filed on Jan. 29, 2004 and serial no. PA 2004 00428 filed on Mar. 17, 2004. The entire contents of these prior applications are incorporated herein by reference.

In a first aspect, the present invention relates to disposable, wearable, self-contained medicine dispensing device comprising a housing and attaching means, preferably adhesive means, for attaching said housing to the skin of a user of said device.

There has been a long felt need for such a device that is compact, reliable, inexpensive, quiet and sturdy.

Such a device is obtained according to the invention by providing the device with a cylindrical medicine container, preferably a carpule, incorporating a piston and arranged in said housing, the container having an open distal end and a proximal end closed by a closure body made of a material, preferably silicone, that can be perforated by a needle, a first hollow needle extending from a first end in the interior of said medicine container through said plug to a second end, a catheter in fluid communication with said second end and for injection of said medicine into said user, said catheter being associated with said housing, a piston rod with a longitudinally extending first screw thread on the outer surface thereof and arranged for displacing said piston from said distal end to said proximal end, a toothed or ratchet wheel having a central aperture for receiving said piston rod and provided with a second screw thread meshing with said first screw thread such that rotation of said ratchet wheel in a first rotational direction will displace said piston towards said proximal end, a pivotable body, preferably a plate element, arranged pivotable around an axis adjacent said ratchet wheel and provided with a pawl for engaging the teeth of said ratchet wheel such that pivoting of said pivotable body in a second rotational direction rotates said ratchet wheel in said first rotational direction, a spring means adapted and arranged for applying a spring force to said pivotable body at a first point spaced from said axis for pivoting said pivotable body in said second rotational direction, and a battery powered actuator for rotating said pivotable body in a third rotational direction opposite said second rotational direction.

In the currently preferred embodiment of a device according to the invention said actuator comprises a shape memory alloy wire and the actuator preferably comprises a shape memory thread or wire fixedly attached at one end to an electrically conducive fastening means and fixedly attached at the opposite end to said pivotable body at a second point spaced from said axis such that contraction of said shape memory wire pivots said pivotable body in said third rotational direction.

Preferably, the spring means comprises a rod spring extending generally parallel with said cylindrical medicine container and having one end fixated against lateral movement and the opposite end abuts, attached to or integral with said first point on said pivotable body.

Advantageously, the second point is located such relative to said axis and said shape memory alloy wire force that the moment arm relative to said axis of the force exerted on said pivotable body by the contraction of said shape memory wire increases as said pivotable body rotates in said third rotational direction and/or the first point is located such relative to said axis and said spring force that the moment arm relative to said axis of said spring force increases as said pivotable body rotates in said second rotational direction.

In the currently preferred embodiment of a device according to the invention, controlling means for controlling the operation of said actuator according to a programme are arranged in said housing.

In the currently preferred embodiment of a device according to the invention the device comprises a dispensing assembly interconnected with said housing, said dispensing assembly comprising:
  a second needle for perforating the skin of said user arranged displaceable along a linear trajectory generally orthogonal to the longitudinal extent of said first hollow needle,
  a plug of a perforatable material, preferably silicone, located on said trajectory and traversed by said first hollow needle,
  a compartment arranged adjacent said plug and receiving said second end of said hollow needle, and
  a guide body having an interior guide passage aligned with and in direct fluid communication with both the lumen of said catheter and said compartment and arranged such that said interior passage and said lumen is on said trajectory.

In a second aspect, the present invention relates to a fillable, disposable, wearable, self-contained medicine dispensing device comprising
  a housing,
  attachment means, preferably adhesive attachment means, for attaching said housing to the skin of a user of said device,
  a cylindrical medicine container, preferably a carpule, incorporating a piston and arranged in said housing, the container having an open distal end and a proximal end closed by a closure body made of a material, preferably silicone, that can be perforated by a needle,
  a hollow needle extending from a first end in the interior of said medicine container through said plug to a second end outside said housing, and
  first displacement means connected to said piston and adapted for displacing said piston from said proximal end towards said distal end, and
  second displacement means comprising a battery powered actuator for displacing said piston from said distal end towards said proximal end.

Hereby it is achieved that the same standard dispensing device may be used for dispensing various types of medicine and that a device without medicine inside and having a longer shelf life than a device incorporating medicine may be filled from a container with a shorter shelf life.

Preferably, the first displacement means comprise a rod attached at one end to said piston and extending through the lumen of said cylindrical container, out through said open distal end and through an aperture is said housing to the other end located outside the housing and provided with gripping means, for instance a handle and the rod is preferably releasably connected to said piston.

In the currently preferred embodiment of a device according to the invention the rod comprises two releasably interconnected rods, one of which is fixedly connected to said piston, the other of which being provided with said gripping means.

In the currently preferred embodiment of a device according to the invention the rod provided with gripping means is provided with a longitudinally extending venting channel for venting air displaced by displacement of said piston from said proximal end to said distal end and a venting aperture is provided in said housing for venting air displaced by said displacement of said piston from said proximal end to said distal end, flow of water into said housing through said venting aperture being obstructed by flow obstructing means such as a one-way or non-return valve or an air permeable, liquid impermeable, hydrophobic membrane.

In a further aspect, the present invention relates to a combination of
- a fillable, disposable, wearable, self-contained medicine dispensing device comprising:
  - a housing comprising first engagement means,
    - attachment means, preferably adhesive attachment means, for attaching said housing to the skin of a user of said device,
    - a cylindrical medicine container, preferably a carpule, incorporating a piston and arranged in said housing, the container having an open distal end and a proximal end closed by a closure body made of a material, preferably silicone, that can be perforated by a needle, and
  - displacement means comprising a battery powered actuator for displacing said piston from said distal end towards said proximal end, and
- a filling adapter comprising:
  - a rectilinear channel extending through said adapter for receiving and guiding a needle of a hypodermic syringe, and
  - second engagement means for releasably engaging said first engagement means of said housing with said adapter located in such an engaged position relative to said housing that said needle when extending through and guided by said channel will perforate said closure body of said carpule for allowing injection of medicine from said syringe into said carpule.

Advantageously, said adapter is provided with locking means for locking said needle inside said channel.

In the currently preferred embodiment of a combination according to the invention
- said adapter is provided with a fixedly arranged hollow venting needle extending parallel with said channel, and
- said housing is provided with a venting element made of a material that can be perforated by said venting needle,
- the location of said venting element in said housing and of said venting needle in said adapter being such that said venting needle will extend through said venting element into the interior of said housing when said adapter is in said engaged position.

Preferably, said venting element is constituted by an 0-ring arranged around said carpule at said proximal end thereof.

In a yet further aspect, the present invention relates to a medicine filling adapter comprising the features of the filling adapter of the combination according to the invention.

In a yet further aspect, the present invention relates to a method of filling medicine into a fillable, disposable, wearable, self-contained medicine dispensing device comprising the following steps:
- providing a fillable, disposable, wearable, self-contained medicine dispensing device comprising:
  - a housing,
    - attachment means, preferably adhesive attachment means, for attaching said housing to the skin of a user of said device,
    - a cylindrical medicine container, preferably a carpule, incorporating a piston and arranged in said housing, the container having an open distal end and a proximal end closed by a closure body made of a material, preferably silicone, that can be perforated by a needle, and
  - displacement means comprising a battery powered actuator for displacing said piston from said distal end towards said proximal end,
- providing a hypodermic syringe containing said medicine,
- perforating said closure body with the needle of said syringe, and
- pressing said medicine into said carpule such that said piston is displaced from said proximal end towards said distal end.

In a yet further aspect, the present invention relates to a disposable, wearable, self-contained medicine dispensing device comprising a housing having an aperture and an interior compartment communicating with said aperture and adapted for receiving a cylindrical medicine container, preferably a carpule, the container incorporating a piston and having an open distal end and a proximal end closed by a closure body made of a material, preferably silicone, that can be perforated by a first hollow needle, a piston rod displaceably arranged in said housing for displacing said piston from said distal end to said proximal end when said container is received in said compartment, and displacing means adapted for displacing said piston rod and comprising a battery powered actuator, preferably wherein said housing adjacent said aperture is provided with first interconnecting means for interconnecting said hosing with second interconnecting means provided on a catheter assembly comprising said first hollow needle adapted for being inserted into said closure body when said carpule is received in said compartment and said first and second interconnecting means are mutually engaged for interconnecting said housing and said catheter assembly such that said first hollow needle extends from a first end in the interior of said carpule through said closure body to a second end, and a catheter in fluid communication with said second end and for injection of said medicine into said user.

In a final aspect, the present invention relates to a combination comprising:
- a disposable, wearable, self-contained medicine dispensing device as described above,
- a cylindrical medicine container, preferably a carpule, the container incorporating a piston and having an open distal end and a proximal end closed by a closure body made of a material, preferably silicone, that can be perforated by a first hollow needle, and
- a catheter assembly comprising:
  - said first hollow needle adapted for being inserted into said closure body when said carpule is received in said compartment and said first and second interconnecting means are mutually engaged for interconnecting said housing and said catheter assembly such that said first hollow needle extends from a first end in the interior of said carpule through said closure body to a second end, and
  - a catheter in fluid communication with said second end and for injection of said medicine into said user.

In the following, the invention will be explained more in detail in connection with several embodiments of a dispensing device shown solely by way of example in the accompanying drawings where FIG. 1 is a schematic perspective view of a device according to the invention, FIG. 2 is an exploded view of the components in the housing in FIG. 1, FIGS. 2a-2e are enlarged scale views of different aspects of the flexible piston according to the invention shown in FIG. 2

FIGS. 5 and 5a-5c are enlarged scale views of the actuator of FIG. 3 in assembled condition.

Figure 1:
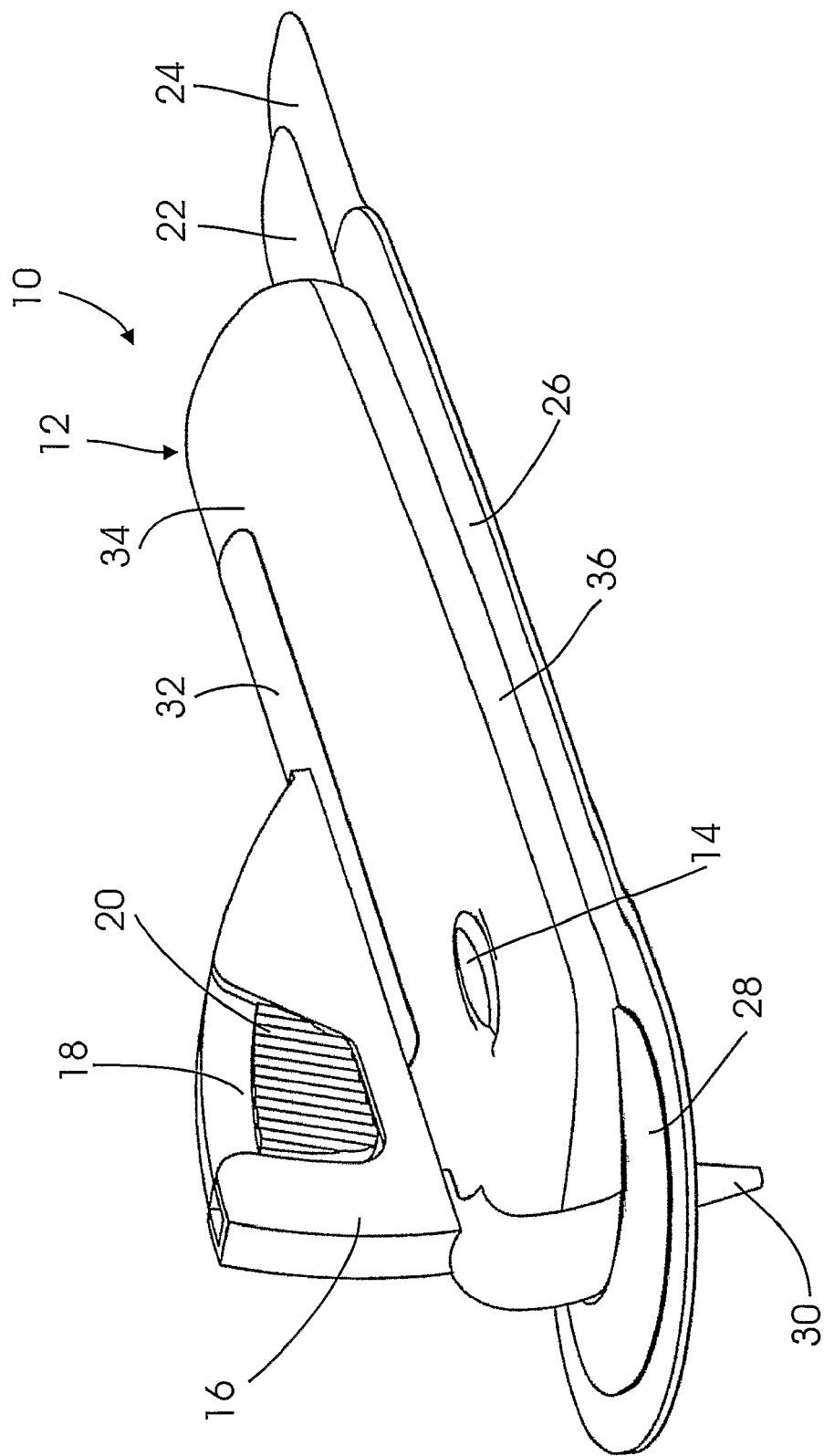
Figure 6:
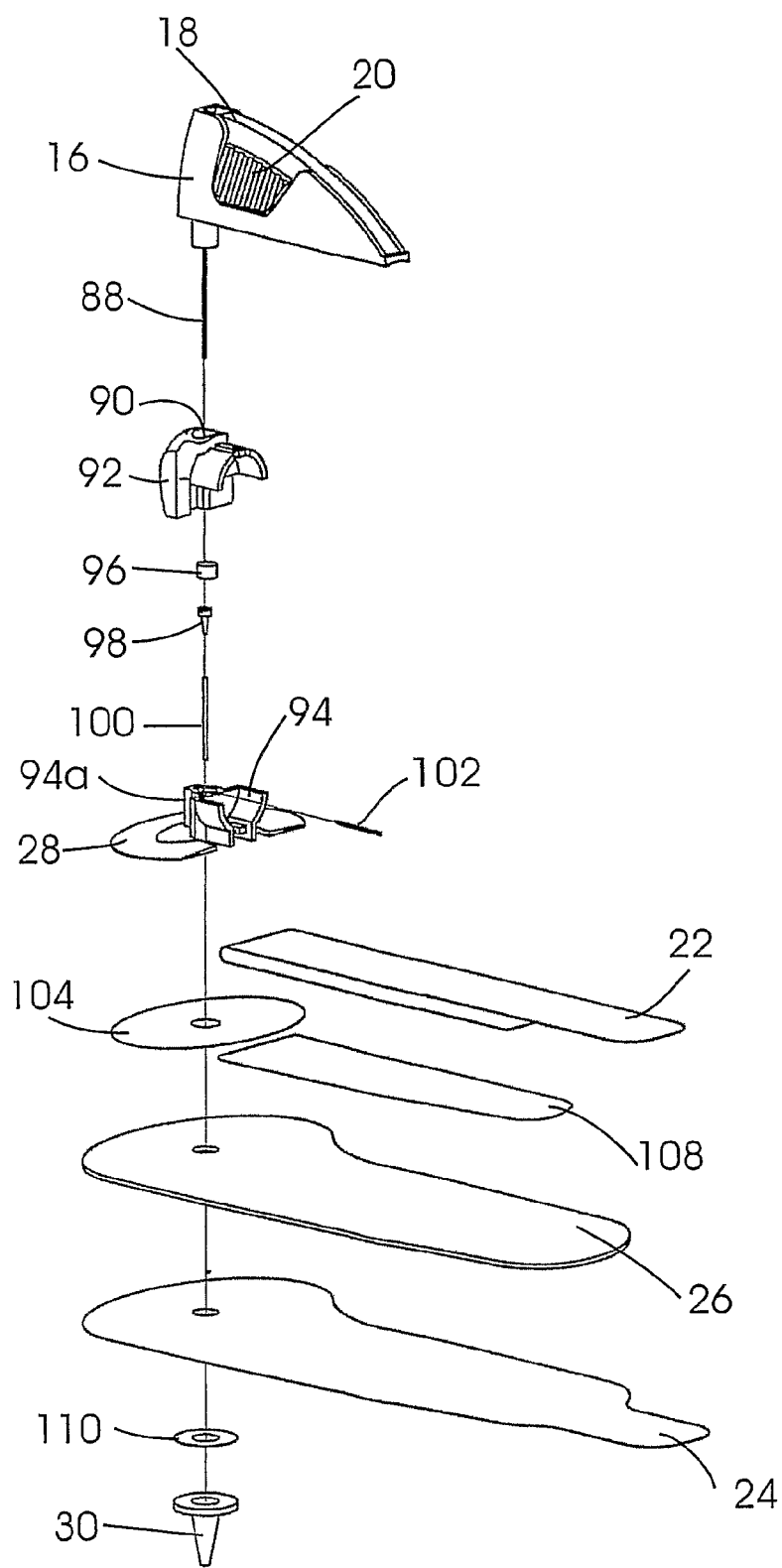
FIG. 6 is a schematic exploded view of the dispensing mechanism according to the invention.
Figure 6C:
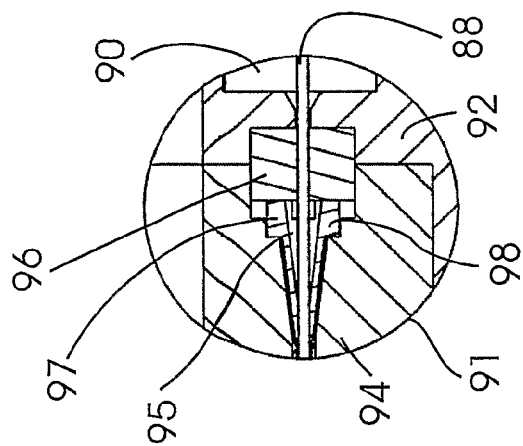
Figure 6B:
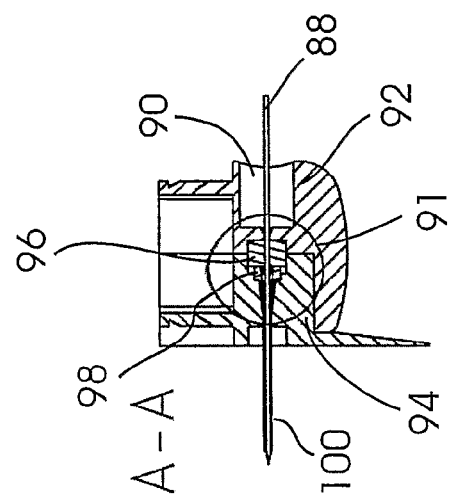
Figure 6A:
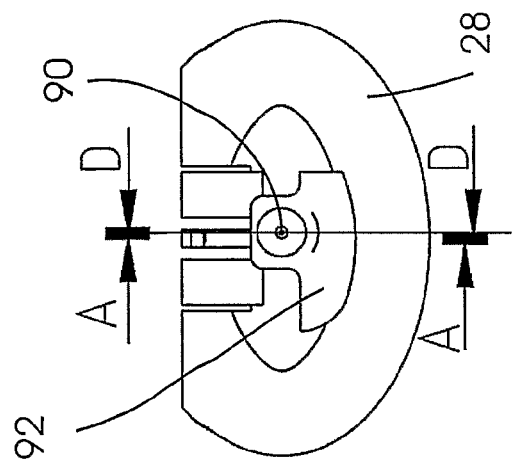
Figure 7A:
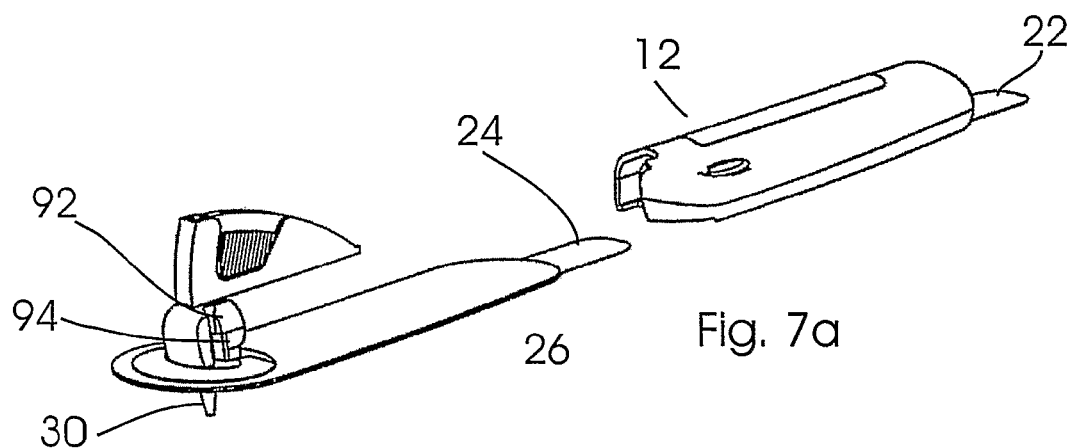
Figure 7B:
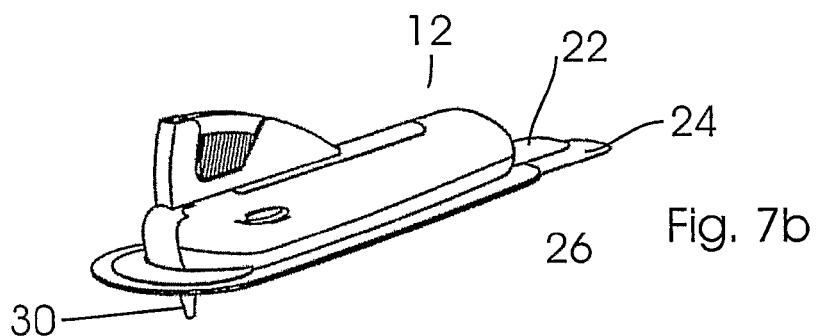
Figure 7C:
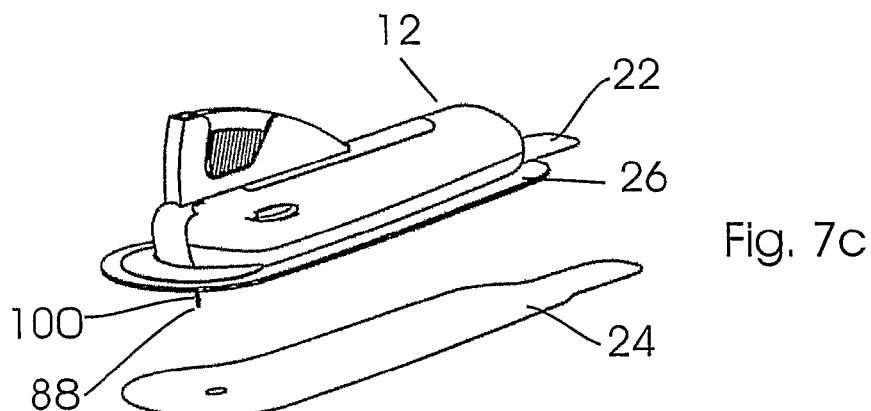
Figure 7D:
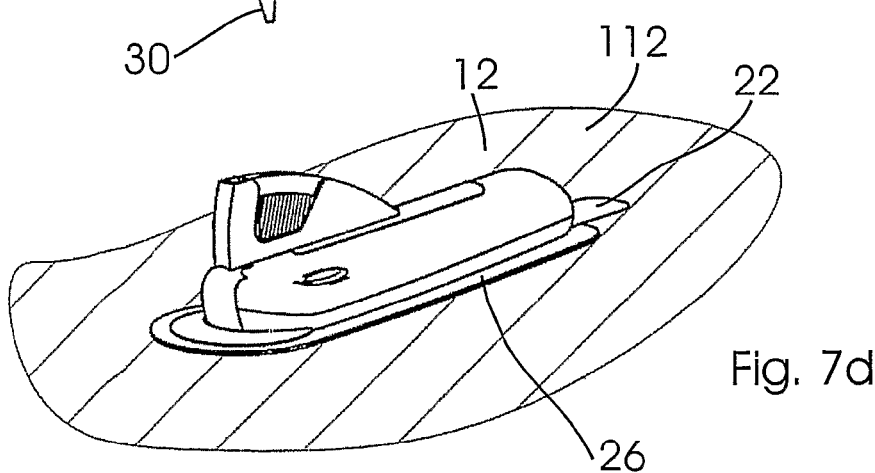
Figure 7E:
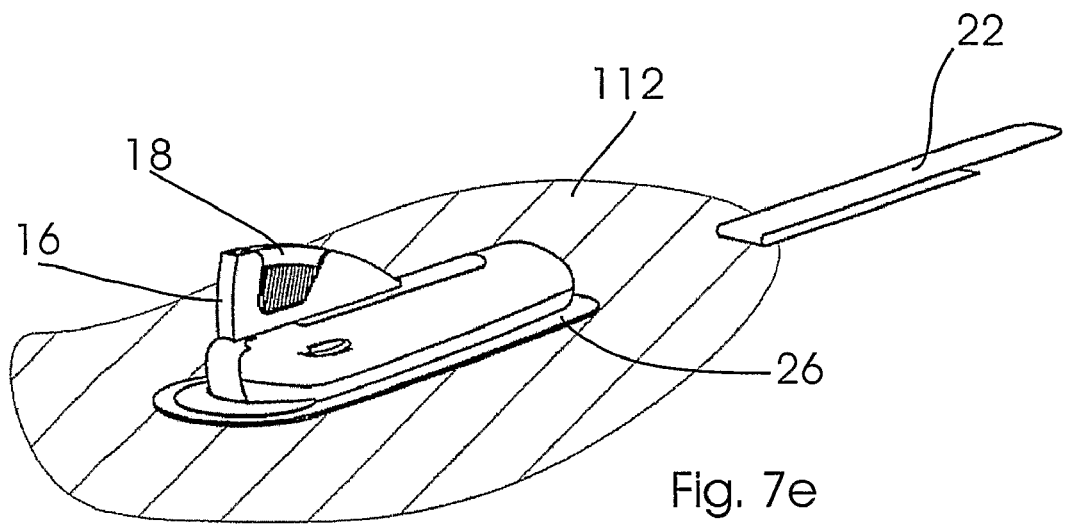
Figure 7F:
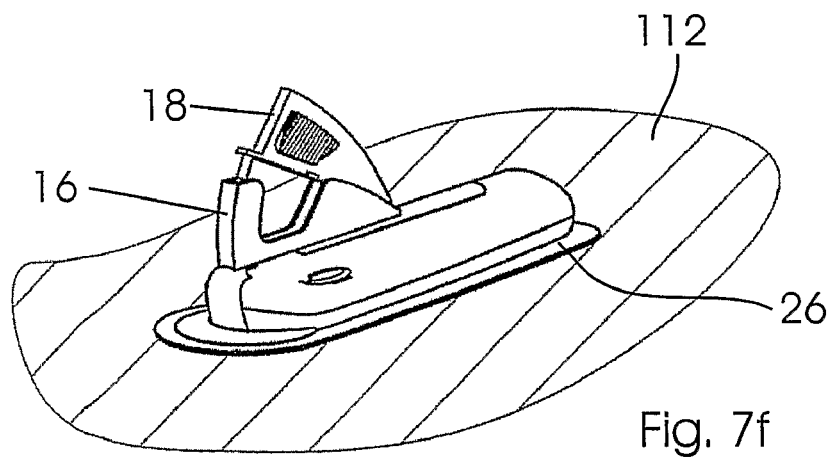
Figure 7G:
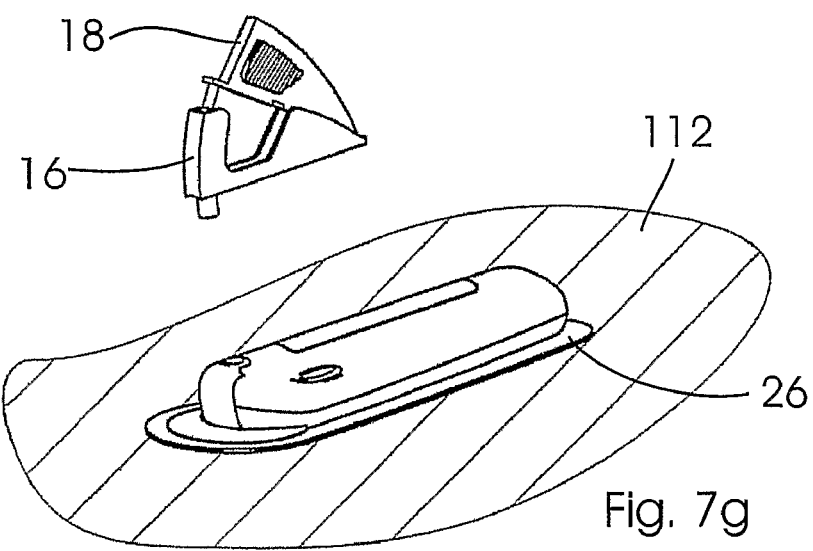
Figure 8:
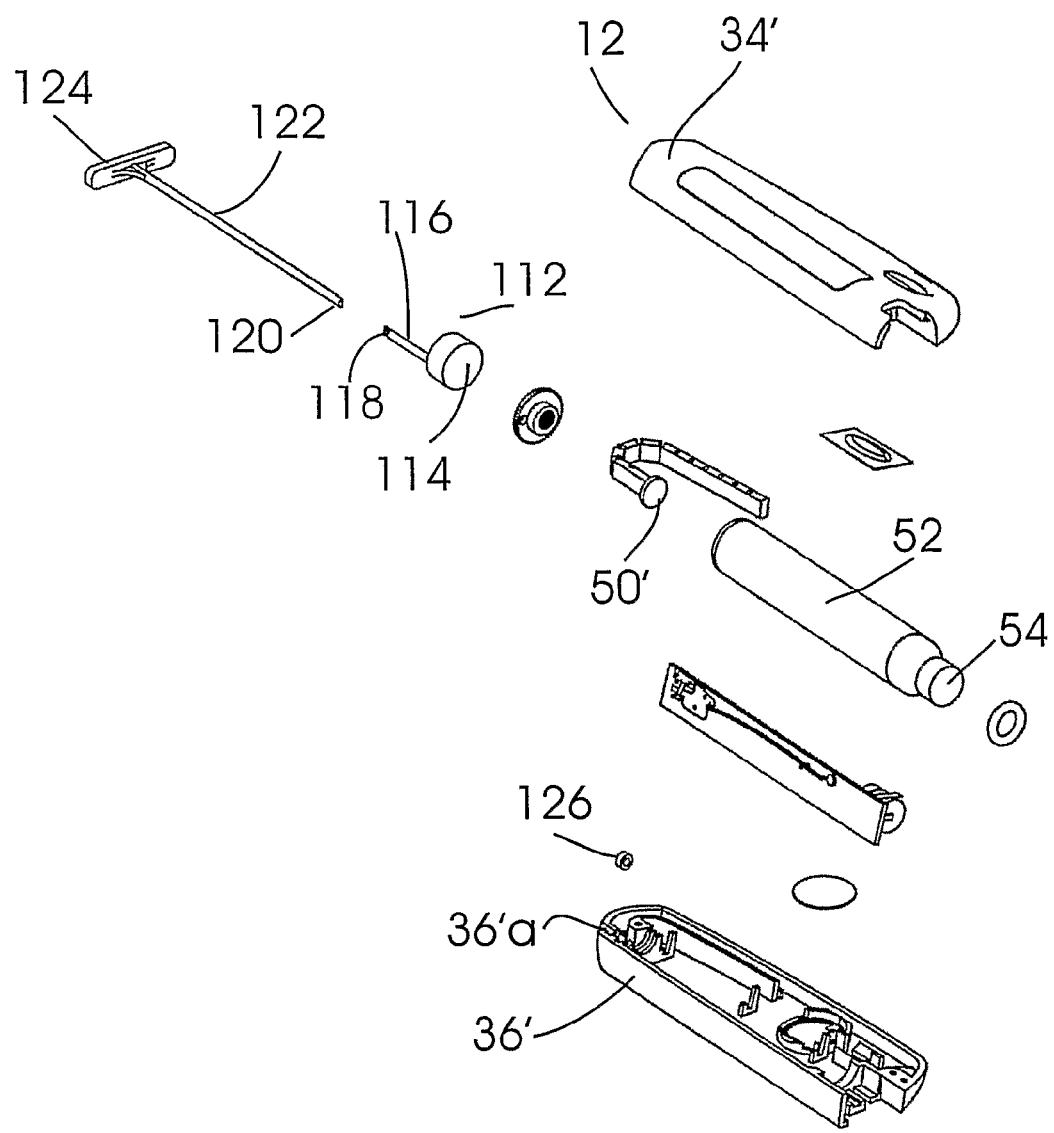
Figure 14:
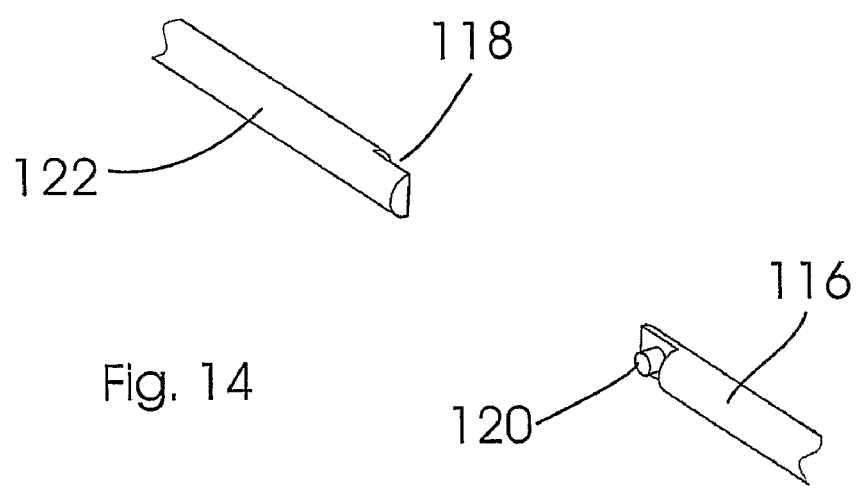

FIGS. 6a-6k are enlarged scale views of details of the fluid flow path of the medicine, FIGS. 7a-7g are views illustrating the application of the dispenser of FIG. 1 to the skin of a user of the device, FIG. 8 is a schematic exploded view of a fillable medicine dispenser according to the invention, FIGS. 9-13 are schematic partially cut away views of the fillable dispenser of FIG. 8 illustrating the operation thereof, FIG. 14 is an enlarged scale view of the releasable connection of the pulling rod in FIG. 9, FIGS. 15-17 are schematic views illustrating the method according to the invention of filling medicine into a dispensing device according to the invention.

Figure 18:
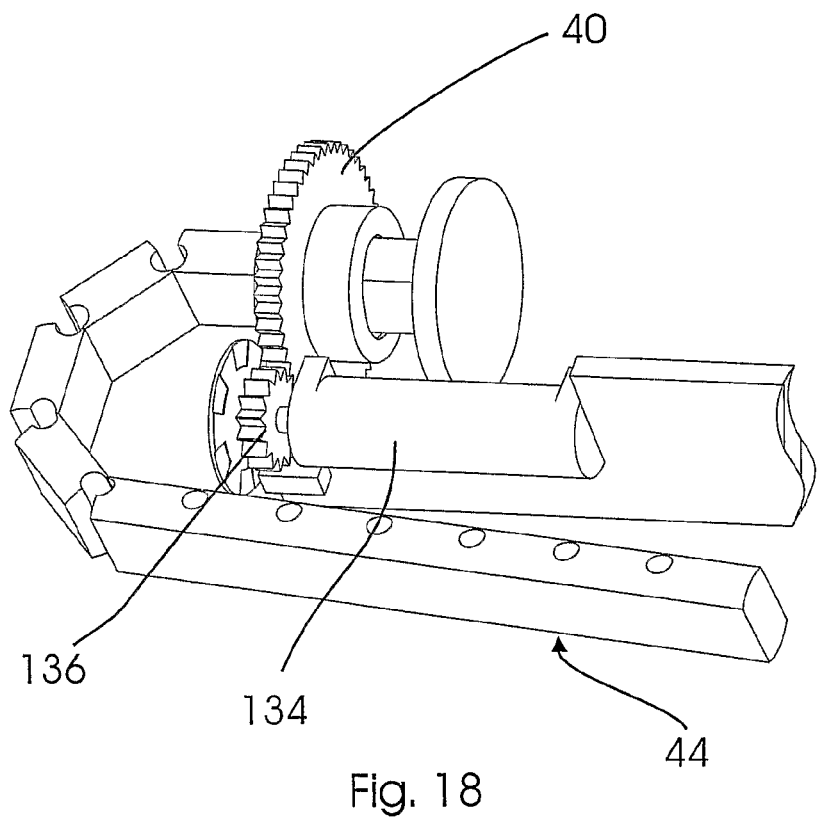

FIG. 18 is an enlarged scale view of an alternative actuator according to the invention, FIGS. 19-23 are schematic views of a combination according to the invention of a filling adapter and a dispensing device according to the invention.

Figure 24:
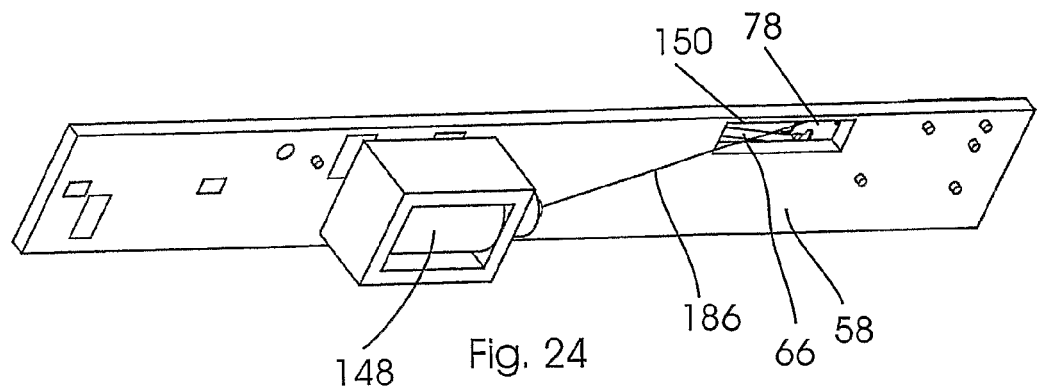
Figure 25:
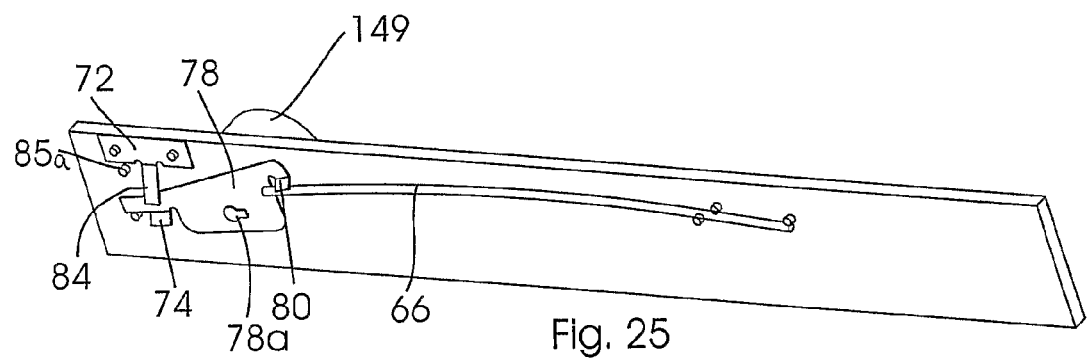
Figure 26:
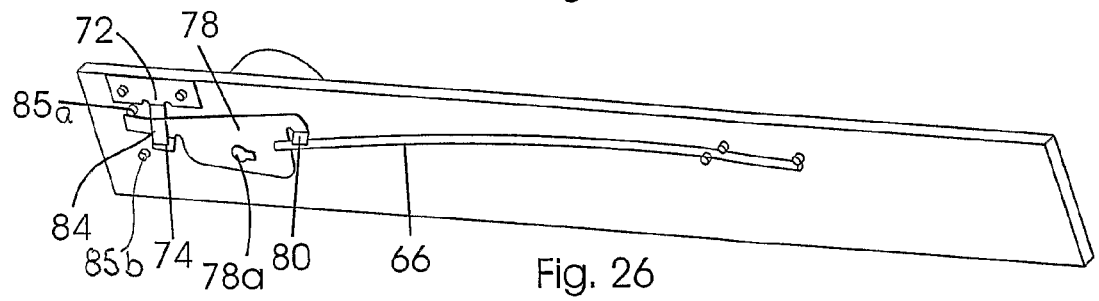
Figure 27:
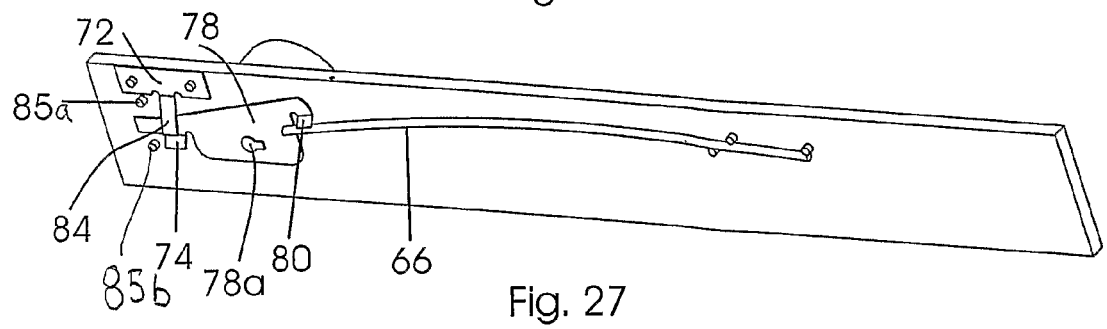
Figure 28:
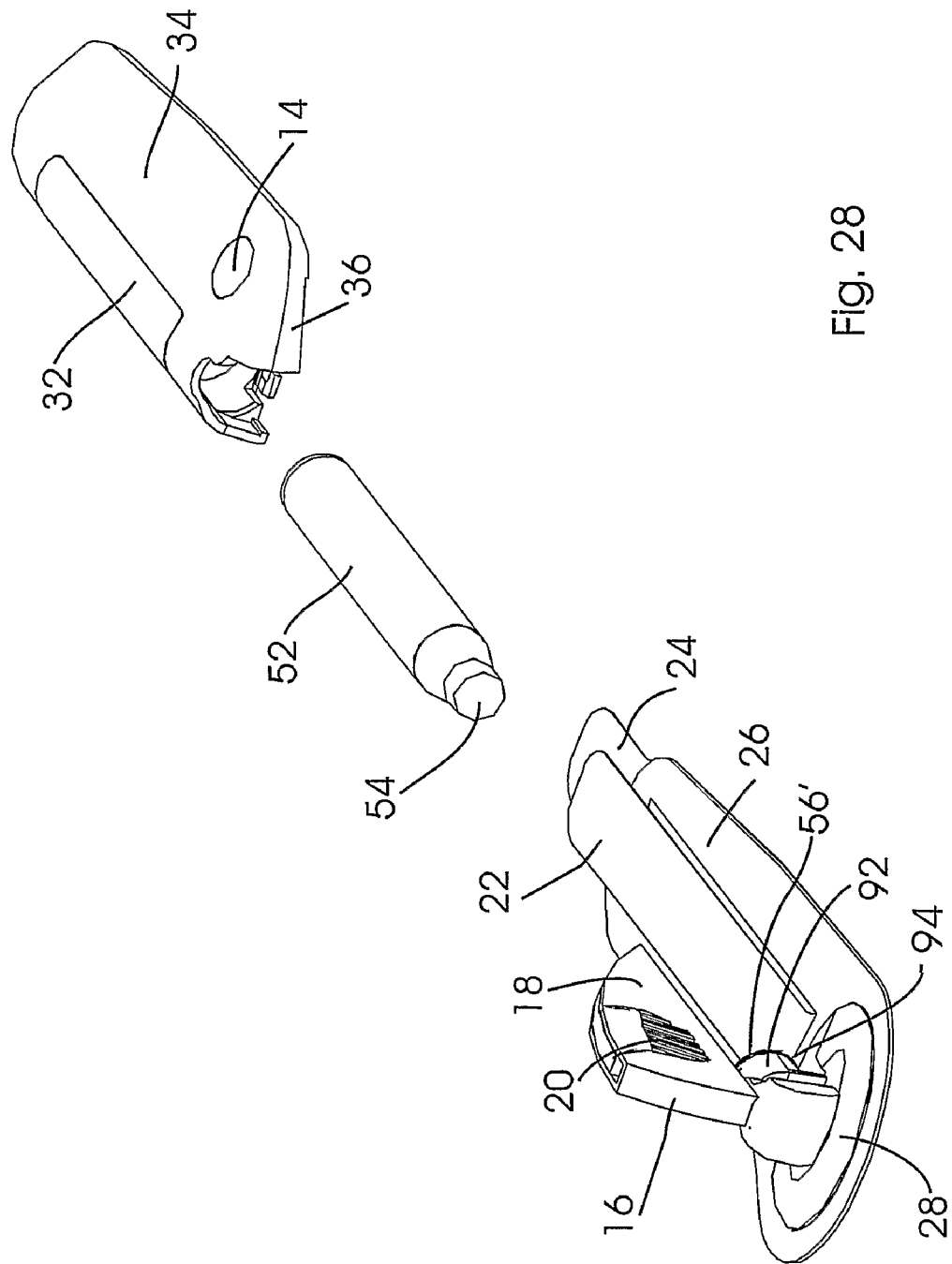
Figure 29:
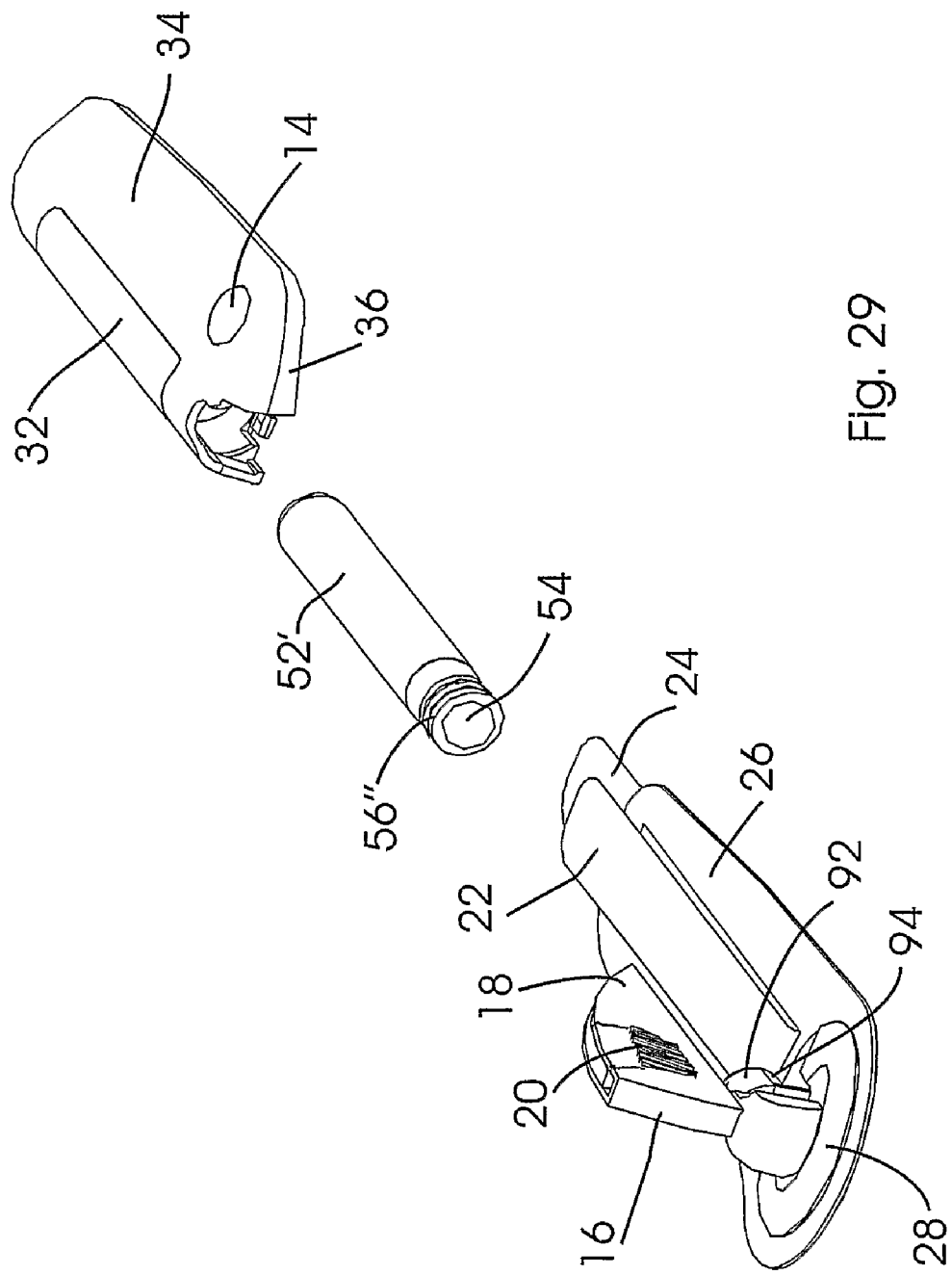

FIG. 24 is a schematic view of further alternative actuator according to the invention, FIGS. 25-27 are schematic views illustrating the operation of a yet further actuator according to the invention, and FIGS. 28-29 are schematic views of a medicine dispenser according to the invention where a separately supplied carpule is inserted in the housing prior to use by a user of the dispenser.

Referring now to FIGS. 1-6, a fully disposable medicine dispensing device according to the invention, generally referenced by the numeral 10, comprises a preferably hermetically sealed housing 12 provided with a push button 14 for activating and deactivating the device as well as activating a so-called bolus operation as explained in the following.

At one end of the housing 12 a stylus or stiletto 16 is mounted. The stylus 16 includes a handle 18 formed with a number of ribs 20 for improved grip. The function of the stylus 16 is illustrated in FIGS. 6-7 and is described in the following.

The housing 12 comprises a top part 34 and a bottom part 36. At the bottom part 36 of the housing 12, a foil 22 is attached. An adhesive pad 26 is provided including a skin friendly adhesive material for fixating the device 10 relative to the skin surface part of a patient or user. The adhesive material may for instance be chosen within the well known field of ostomy pouches, see for instance European patent application No. 0 413 250 and European patent application No. 0 092 999. Reference is made to the mentioned European patent applications and the patent applications are hereby incorporated by reference.

On surface of the adhesive pad 26 facing the skin surface a release film 24 is adhered for protecting the adhesive surface of the pad 26 such that the adhesive properties are intact when the pad 26 is to be adhered to the skin of a user of the dispensing device 10.

In use, the user removes the protective slip release film 24, thereby exposing the adhesive pad, which is then adhered to the abdominal skin of the user.

The stylus 16 includes a sharp needle 88 (see FIG. 6), which is initially protected by a protection cap 30, which the user removes prior to the application of the dispensing device 10, preferably to the abdominal skin of the user.

The top part 34 of the housing 12 includes a window 32 for the user to inspect the level of medication left in a container 52 or carpule located inside the housing 12.

Figure 2:
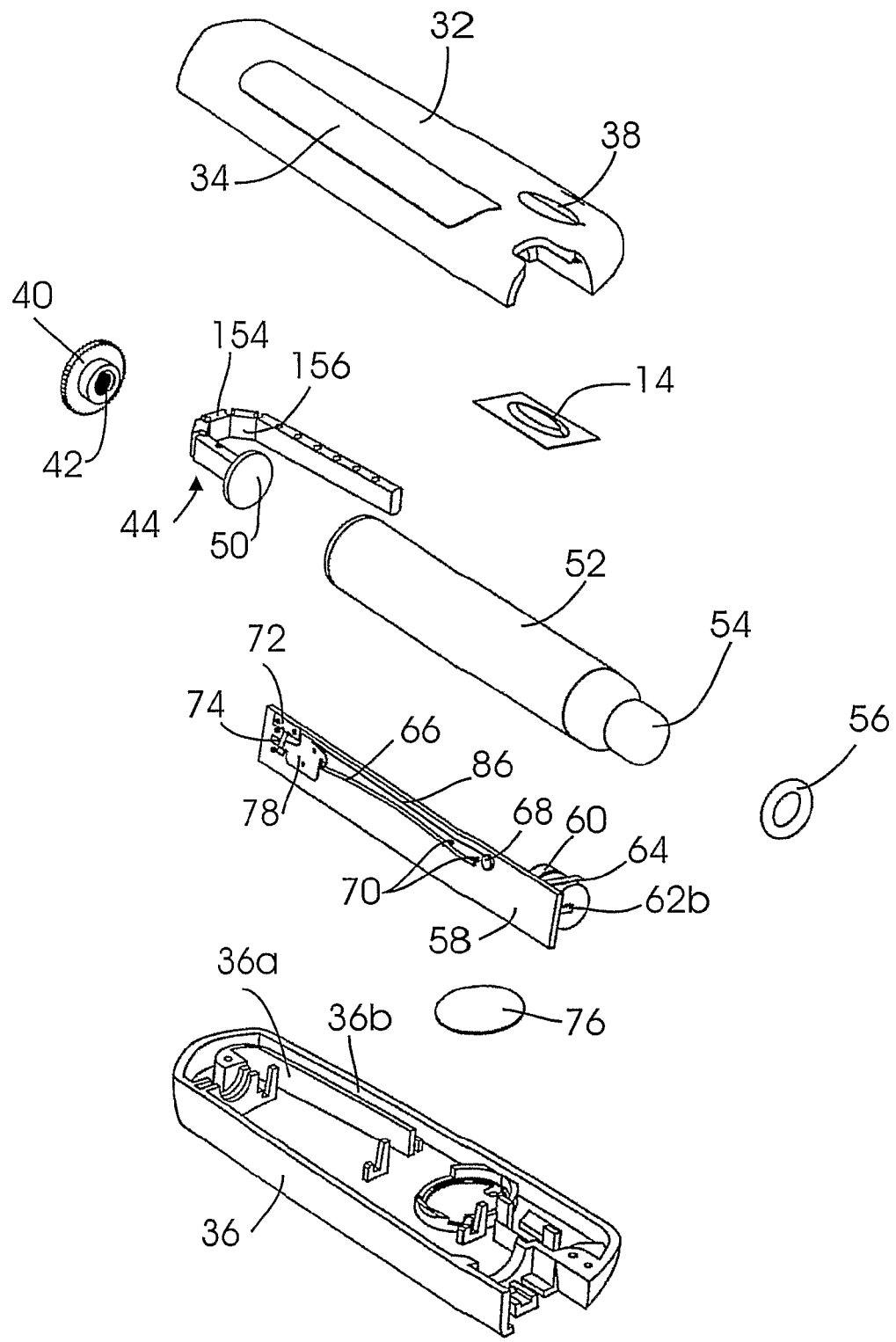
Figure 3:
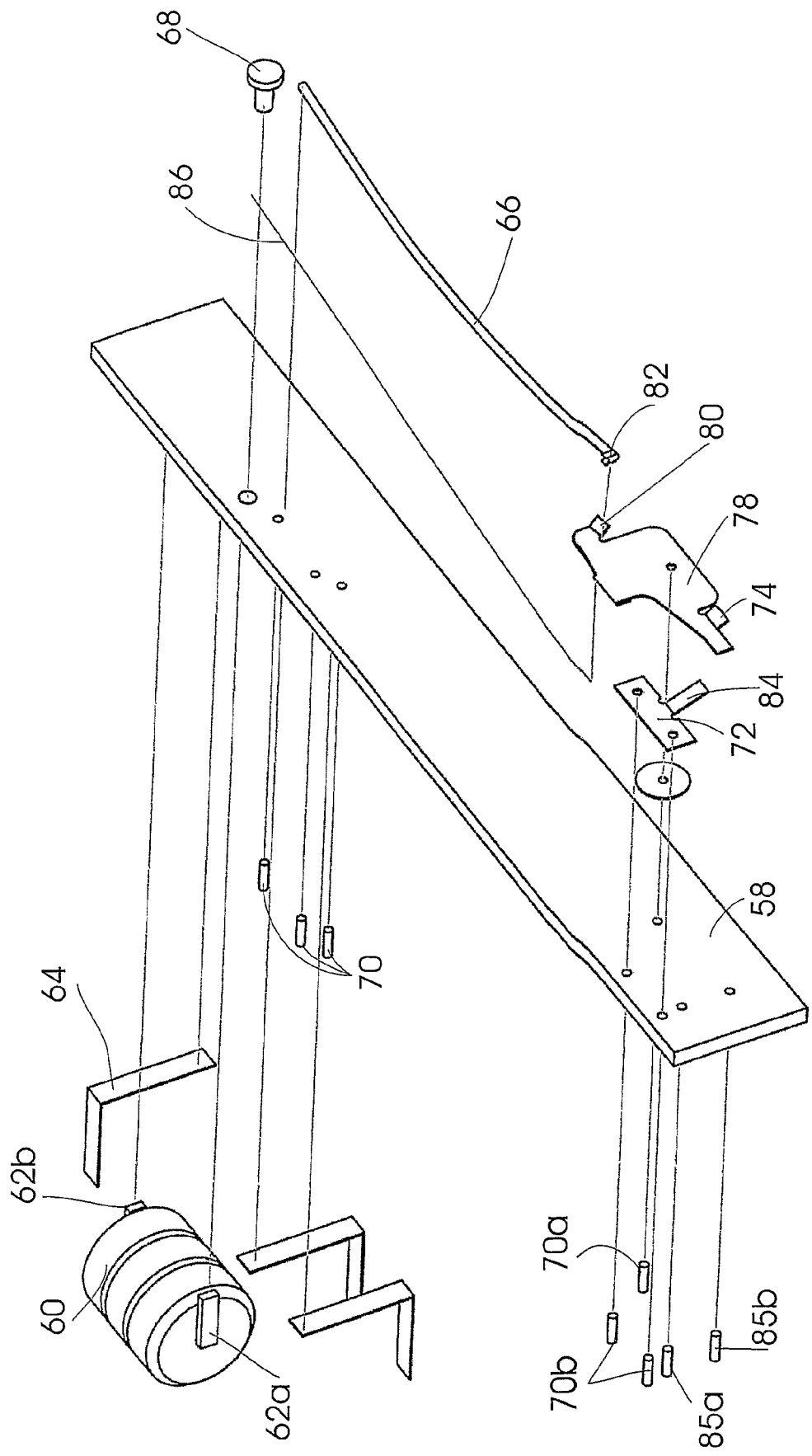
FIG. 3 is a schematic enlarged scale exploded view of the shape memory actuator according to the invention shown in FIG. 2
Figure 4:
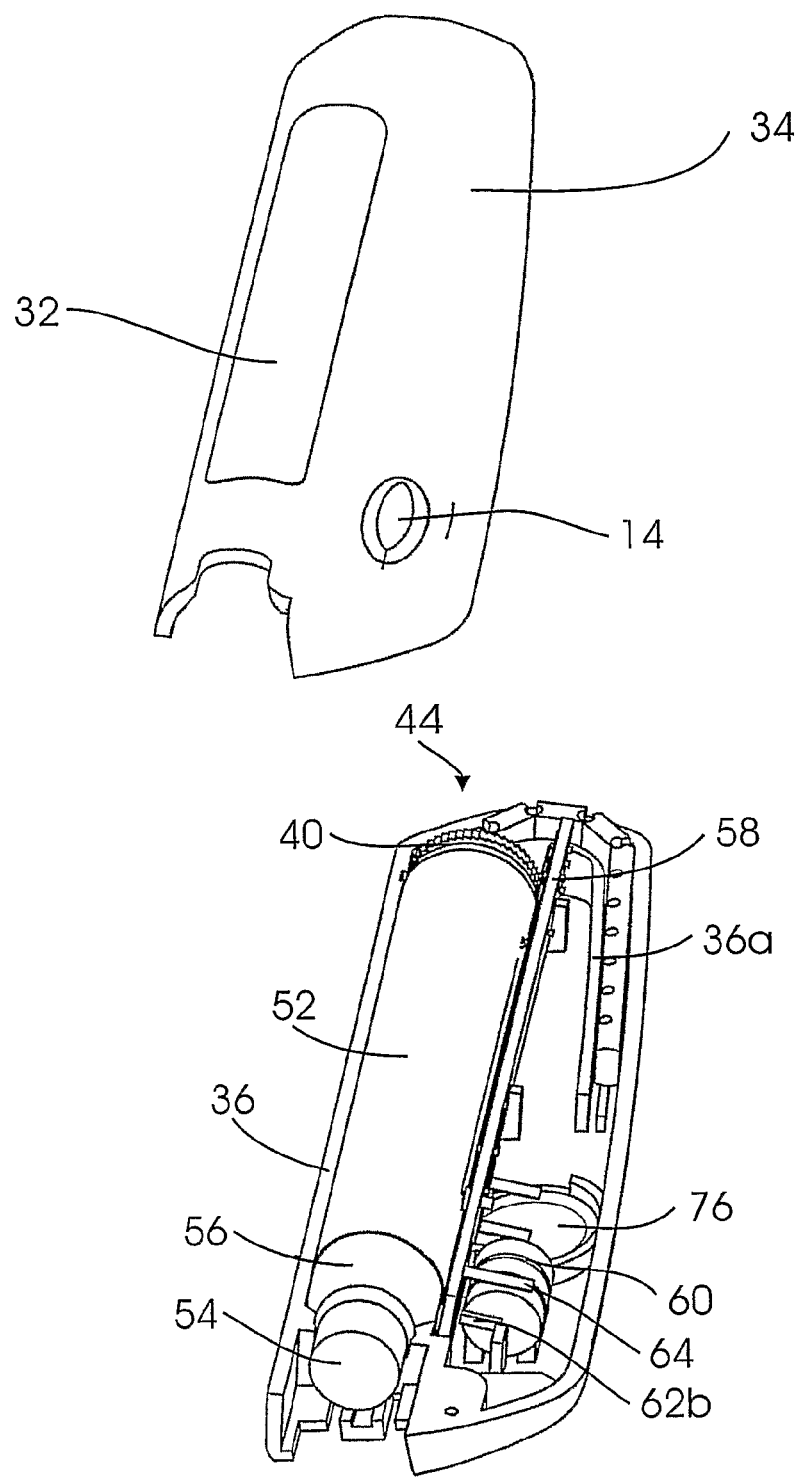
FIG. 4 is a view of the components in FIGS. 2 and 3 in assembled condition.

FIGS. 2 and 3 are exploded views of the components of the medicine dispensing device according to the invention. The components shown in exploded view in FIGS. 2 and 3 are shown in FIG. 4 assembled inside the bottom part 36 of the housing.

Referring now to FIG. 2, the push button 14 extends through an opening or aperture 38 in the top part 34 of the housing 12. The window 32 in the top part 34 is illustrated as being oblong, but may have any geometrical configuration such as elliptical, circular, square, alternatively a plurality of windows may be formed in the top part 34, alternatively the window may be formed in bottom part 36, further alternatively either the top part 34 or the bottom part 36 may be made from a transparent plastic material.

The housing 12 contains a glass or plastic container or carpule 52 for storing and dispensing medicine such as insulin. The container or carpule 52 is of a well-known type having a perforatable dispensing projection 54 for receiving a catheter. The projection 54 has a perforatable portion made of an elastomer, for instance silicone, and is hermetically mounted in the bottom part 36 by means of an O-ring 56 of silicone.

A toothed wheel or ratchet wheel 40 is mounted inside the housing 12 for driving a piston or plunger 50 into one end of the carpule 52 for dispensing the contents of the carpule 52 through the dispensing projection 54. The toothed wheel 40 includes an aperture 42 for receiving a threaded bar or flexible piston rod 44.

The piston 50 is attached to one end of the flexible piston rod 44 constituted by a series of elements 154 interconnected by hinge means 156 (see FIGS. 2b-2d) and arranged for movement between two guide walls. The flexible piston rod 44 is made of plastic material to keep the weight down and to allow cheap and simple manufacture by injection moulding. Axial displacement of the piston 50 will press medicine, for instance insulin, out of the carpule 52 into the catheter assembly described more in detail in the following.

The elements 154 are integral with each other by means of hinges 156 which allow adjacent elements to pivot relative to one another from the position abutting one another shown in FIG. 2b wherein the elements 154 together form a rectilinear piston rod with abutment surfaces 155 and hinges 156 affording rigidity and thus rendering the piston rod 44 capable of exerting a pressure on the piston 50 in the carpule without deflecting laterally, to the position shown in FIG. 2d wherein the elements are pivoted way from one another so as to allow the curvature of the piston rod 44 which allows the compact configuration of the device with the initially major part of the piston rod extending along the length of the carpule 50 between walls 36a and 36b of the bottom part 36 of the housing.

The material of the flexible piston rod 44 is any suitable mouldable material, but it is preferred that the material is a plastic material such as Nylon, PA or POM because of possibility of precise manufacture and low friction as well as low cost, low weight and re-cycling issues.

Each element 154 is provided with exterior threads 158 on two opposed portions 162 and 164 of the elements having a circular cylindrical configuration for allowing an internal thread of the ratchet wheel 40 (FIG. 2) to mesh therewith such that rotation of the ratchet wheel 40 will displace the piston rod 44 into the carpule 52. At least the side of the elements 154 coinciding with the hinges 156 is flat to allow practical moulding of the hinge. The flat side or flat opposed sides also allows preventing rotation of the piston rod 44 around its axis when being axially displaced by the internal thread of the ratchet wheel 40.

The displacement of the rod 44 and piston 50, by rotation of the toothed wheel 40 counter clock-wise, towards the dispensing projection 54 will press the medicine contained in the carpule 52 into a catheter tube 100 so that the medicine may be injected into the patient wearing the device. The toothed wheel 40 is rotated, and the rod 44 thereby displaced, by means of a shape memory alloy, SMA, actuator, described more detailed in the following. Reference is made patent applications U.S. Ser. No. 10/622,065 and WO 02/057627 in which SMA actuators are also described, both applications being hereby incorporated in the present description by reference.

The displacement of the flexible piston rod 44 takes place in the following manner: A conveying pawl 74 of a plate 78 pivotably mounted on a pin 70a engages the teeth of the toothed wheel 40 such that the toothed wheel 40 is rotated when the plate 78 pivots counter clock-wise, the internal threads in aperture 42 thereby being rotated for displacing the flexible rod and the plunger 50 further into the carpule 52. The conveying pawl 74 is operated by an SMA actuator, described more in detail in the following. The conveying pawl 74 is operatively connected to an elongated rod spring 66. The spring 66 is held in place by a number of pins 70 at one end thereof.

A battery 60 is provided and is fixated to a printed circuit board 58 by a number of holding pins 64. Electrical conductive pins are provided to the positive and negative poles of the battery 60, respectively, for the supply of electrical power to the elements attached to the printed circuit board 58.

A beeper 76 is also mounted in the housing 12. The beeper 76 may be used for communicating status information or alarms to the user. The beeper 76 is electrically fed by the battery 60.

Referring now to FIG. 3, that is an exploded view of the elements attached to or mounted on the PCB 58, the SMA actuator is illustrated. In the presently preferred embodiment of the invention, the SMA actuator comprises an SMA (Nitinol) thread or wire 86 connected at one end to the battery terminal 62a by means of a terminal pin 68 and connected at the other end to the plate 78 such that an electrical current may be applied through the SMA wire 86 through terminal 62a, terminal pin 68, plate 78, spring 66, not shown circuit breaker on PCB 58 controlled by a programmable unit, and finally terminal 62a of battery 60 The electrical current may also be led through pivot pin 70a to said circuit breaker. Also illustrated are details regarding the pivotable plate 78 whereon the conveying pawl 74 is formed.

Opposite the conveying pawl 74 a pawl 80 for engaging the spring 66 is formed in the plate 78. At the end of the spring 66 engaging the pawl 80, a projection 82 of the spring is formed so as to improve the transference of forced from the spring 66 to the pawl 74.

A stop pawl 84 of a plate 72 is provided for engaging the ratchet wheel engaging and stopping the ratchet wheel 40 against rotation clock-wise. The plate 72 is fixedly attached to the PCB 58 by means of pins 70b.

FIG. 4 is a view of the device wherein the components have been assembled inside the housing 12.

FIGS. 5a-5c are enlarged views of the encircled portion X in FIG. 5 illustrating the operation of the SMA actuator and the toothed wheel 40.

FIG. 5a illustrates the initial position of the plate 78 where a projection 78a thereof abuts a stop pin 85b. The plate 78 is engaged by the rod spring 66 exerting an upwardly orientated force on the plate 78 forcing the projection 78a against the stop pin 85b. No electrical current is applied to the NITI thread 86 and the thread is therefore in its expanded or uncontracted state.

When electrical current is applied to the thread 86 as discussed above, the thread 86 is heated and, due to the physical properties of the material, the thread contracts when the temperature is increased beyond a certain value thereby pivoting the plate 78 clock-wise and tensioning the rod spring 66.

This is illustrated in FIG. 5b where the thread 86 has contracted and thereby has pivoted the plate 78 clock-wise so that the free end of the spring 66 is depressed by the pawl 80 and the conveying pawl engages 74 the next tooth on the toothed wheel 40. The clock-wise rotation of the plate 78 is limited by the pin 85a on the PCB 58.

FIG. 5c illustrates an intermediate situation after turning off electrical current to the thread 86, thereby causing the thread 86 to expand and consequently release its pull on the plate 78 whereby the force exerted by the spring 66 forces the plate 78 to pivot counter clock-wise to the configuration illustrated in FIG. 5a.

The toothed wheel 40 is thereby rotated counter clock-wise by the pawl 80 and consequently the piston or plunger 50 is displaced further into the carpule 52. The stop pawl 84 engages the next tooth on the toothed wheel 40 and prevents the pressure in the carpule 52 from pressing the piston 50 backwards and thereby pivoting the wheel 40 clock-wise.

If the rod spring 66 were eliminated such that the SMA thread 66 is attached to the plate 78 at a lower point relative to the pivot pin 70a such that contraction of the thread 66 pivots the plate 78 counter clock-wise, i.e. such that the displacement of the piston 50 in the carpule 52 is a direct result of contraction of the thread 66, then there would be a danger of either snapping the thread or damaging the dispensing mechanism because of pressure overload.

The contraction of the thread 66 is rather rapid when the transformation temperature of the alloy is attained. The rate of injection of the medicine into the user is determined by the pressure in the medicine resulting from the displacement of the piston 50. The quicker the rate of injection must be to correspond to the contraction rate of the thread, the higher the pressure is and the higher the tension in the thread is. This may either result in snapping or severely damaging the thread and/or rupturing a component in the dispensing assembly described more in detail in the following.

On the other hand, in the construction according to the invention, by letting the rod spring 66 transfer the displacement force to the plate 78 and thereby to the piston 50, the thread 86 must only flex the spring and rotate the plate 78 alone which can take place very quickly and with a predetermined force having to be exerted by the thread 66, a force which the thread can be dimensioned to exert with no risk of damage. The pumping force exerted by the spring 66 on the plate 78 and thereby the piston 50 is relatively constant and can be designed to achieve the optimal dispensing pressure inside the carpule 52.

The rod spring 66 may be replaced by any suitable resilient body such as a rubber or silicone pad, a tension or compression coil spring, a spiral spring and so on. A particularly advantageous alternative embodiment of the spring 66 is to provide the plate 78 with a projecting rod either fixed to the plate or integral therewith and abutting a stop pin on the PCB 58 at its end remote from the plate 78.

Figure 5D:
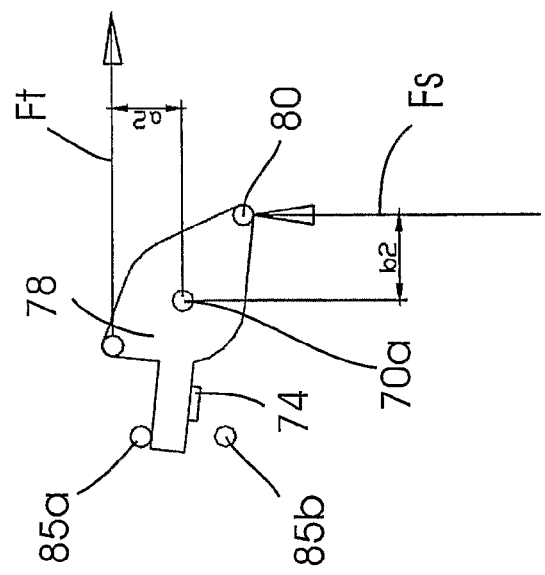
FIGS. 5d-5f are diagrammatical elevational views of the pivotable plate in three different situations illustrating the action of the forces on the plate.
Figure 5E:
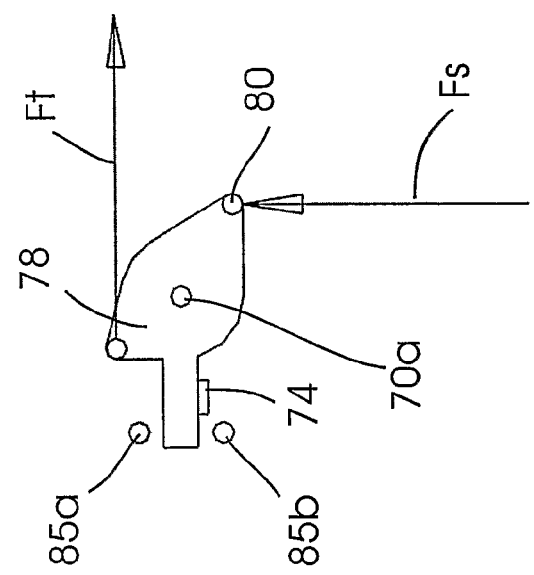
Figure 5F:
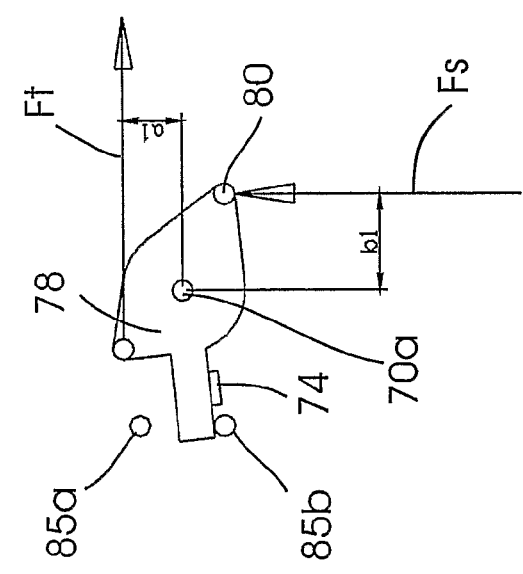

Referring now to FIGS. 5d-5f corresponding to FIGS. 5a-5c, an optimal location of the forces Ft and Fs applied to the plate 78 by the thread 86 and the spring 66 relative to the rotational axis of the plate, the pin 70a, are illustrated.

The moment arm a1 of the thread force Ft in the situation in FIG. 5d, where the thread is just starting to flex the spring 66, is smaller than the moment arm a2 in the situation in FIG. 5f, where the spring 66 has been fully flexed. For a constant value of Fs this entails that the force Ft necessary to flex the spring 66 is smaller when the thread 86 is fully contracted than when it is uncontracted which is advantageous for the effectiveness of the thread and for the useful life thereof.

Analogously, the moment arm b1 of Fs in FIG. 5d, where the spring 66 is the least flexed and therefore where Fs is smallest, is larger than the moment arm b2 in FIG. 5f, where the spring 66 is most flexed and therefore where Fs is largest. Hereby it can be achieved that the moment necessary to flex the spring can be substantially more constant, and the force applied by the plate 78 to the ratchet wheel 40 can be substantially more constant. Both effects are advantageous, one for the performance of the thread 86, the other for achieving a substantially constant dispensing pressure in the carpule 52.

Referring now to FIGS. 6 and 6a-6k, the dispensing mechanism comprises a needle 88 extending downwardly from the stiletto 16 into an opening 90 of a top part 92 for, in co-operation with a bottom part 94, being received in one end of the housing 12. The top part 92 and the bottom part 94 in conjunction form a protecting and guiding sleeve for receiving the dispensing projection 54 of the carpule 52.

As the needle 88 is inserted through the opening 90, the needle passes through a silicone plug 96, ensuring that when the needle 88 is not inserted, no contamination may pass through from the opening 90. The needle 88 passes through the silicone plug 96 and continues into a funnel shaped guide 98 guiding the needle 88 into a catheter tube 100 into the top end of which tube the lower end of the guide 90 is inserted. The catheter tube 100 is made from a soft and flexible material such as PTFE. A catheter needle 102 provides passage of the medicine from the carpule 52 into the catheter tube 100.

An adhesive ring 104 fixates the bottom part 94 to the adhesive pad 26. A plate 28 covers the part of the adhesive ring 104 that extends beyond the bottom part 94. A release foil 22 is adhered to an adhesive pad 108. The adhesive pad 108 serves the purpose of fixating the housing 12 relative to the adhesive pad 26.

The protection cap 30 is fixated to the slip release film 24 by an adhesive ring 110. The protection cap 30 protects the protruding part of the catheter tube 100 and the sharp tip of the needle 88 when shipping or storing the device 10.

FIG. 6a is a top-view of the top part 92 when assembled with the bottom part 94, but without the stiletto 16. FIG. 6b is a view along the line A-A of FIG. 6a. The needle 88 has been inserted in the opening 90 through the plug 96 and extends through the guide 98. The needle 88 further extends through the catheter tube 100. FIG. 6.c is an enlarged view of the circle 91 of FIG. 6b. In the guide 98 a cavity 95 is formed. When the needle 88 is removed, the cavity 95 may receive medication from an aperture 97 formed in the sidewall of the guide 98 (see FIG. 6i). The medication may then flow from the guide 98 into the catheter 100 which, when located correctly, is placed beneath the skin of the patient wearing the device 10.

FIG. 6d shows the assembled top 92 and bottom 94 parts seen from the side from which the needle 102 extends. FIG. 6e is a section along the line B-B of FIG. 6d. FIG. 6f is an enlarged view of the central portion of FIG. 6e. As previously described the medication flows from the carpule 52 through the needle 102. As shown in FIG. 6e the medication flows from the needle 102 into a compartment 99 formed between the plug 96, the inner sidewalls of the top 92 and bottom 94 parts and the guide 98 (see also FIG. 6i). The needle 88 passes through the plug 96 in a direction substantially orthogonal to the direction of the catheter 102, but without intersecting the catheter 102.

FIG. 6g is a section along the line C-C of FIG. 6d while FIG. 6h is an enlarged view of the circle 99b of FIG. 6g. The figure shows the compartment 99 wherein the medication is received from the needle 102. The needle 88 is visible in the background.

FIGS. 6i-6k further illustrate the pathway of the medicine through the needle 102 to the guide 98 into the catheter tube 100 shown by arrows in FIG. 6i.

FIG. 7a illustrates the device prior to the interconnection of the housing 12 with the dispensing assembly being inserted in a receiving part or sleeve formed by a top part 92 and a bottom part 94. This assembly may be performed prior to delivering the device to the user or the process of assembling the two parts may be performed by the user/care-giver.

FIG. 7b illustrates the device 10 assembled. Before the user applies the device, preferably to the abdominal skin, the slip release film 24 is removed, thereby exposing the adhesive pad 26. Along with the slip release film 24, the protection cap 30 is removed, thereby exposing the needle 88. The needle 88 extends through the catheter tube 100. The needle 88 perforates the skin of the patient when the device is placed on the skin surface, thereby the catheter tube 100 is guided beneath the skin of the patient.

FIG. 7d illustrates the device placed on the user's skin 112. After adhering the device to the abdominal skin 112 of the patient, the foil 22 may be removed (see FIG. 7e), thereby fastening or fixating the housing 12 to the adhesive pad 26. This operation may also be performed prior to application of the device to the skin.

In FIG. 7f the user has lifted the handle 18 so that the needle 88 is retracted from the patient, leaving the catheter tube 100 inserted into the skin of, the patient. This enables the device to deliver the medicine subcutaneously to the patient. When the needle 88 has been retracted from the patient, the entire stylus 16 and handle 18 may be separated from the housing 12 of the device 10 since the stylus 16 may hinder or limit the free movement of the patient.

Preferably, when retracted, the needle 88 is fully embedded in the stylus 16 so that no person or persons inadvertently can be pricked by the needle. Alternatively, the tip of the needle 88 may be covered with a plug or stopper after retraction and separation from the device 10.

FIG. 8 is a view of an exploded device according to the present invention wherein the carpule 52 in the device supplied to the user is initially empty and may be filled by the user. The device 10 includes many parts similar to those described in FIG. 2 and these parts will not be discussed further.

The embodiment illustrated in FIG. 8 includes a plunger 112 wherein the plunger head 114 has been fitted with a rod 116 extending backwardly. The rod 116 has an engagement 118 to be engaged by a corresponding engagement part 120 of a second rod 122 including a handle 124 (see FIG. 14). A modified top part 34' and bottom part 36' are used in this embodiment. The parts have been modified for receiving the rods 116 and 122 through an opening 36'a.

When the user receives the device 10', the carpule 52 is empty and the plunger head 114 is located at the end near the protruding part 54 of the carpule 52. The rod 122 extends from the opening 36'a in the housing 12 through an annular seal 126, such as a silicone ring arranged in the opening and surrounding the rod or bar 122 in a way such that the interior of the housing 12 can not be contaminated.

Figure 9:
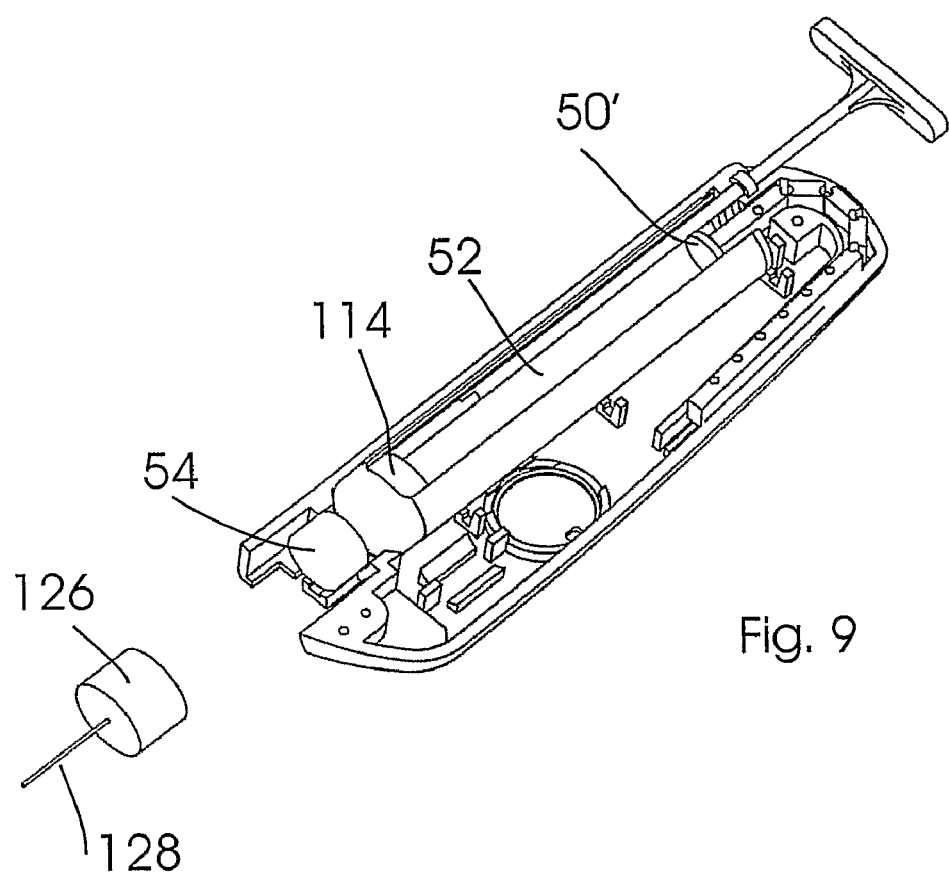

FIG. 9 illustrates the parts of FIG. 8 assembled in the bottom part 36 of the housing 12. The figure illustrates the plunger head 114 in a position near the protruding part 54 of the carpule 52.

In order for the patient or care-giver to fill the carpule 52 with the medication, a bowl or cup shaped adapter 126 shaped to receive the projection 54 is provided with a double pointed needle 128 extending through the adapter 126 so as to establish fluid communication between the interior of the carpule and an external container containing the medication.

The carpule in all the embodiments described herein is coated with a non-toxic lubricant on the inside surface for facilitating the movement of the plunger or plungers.

Figure 10:
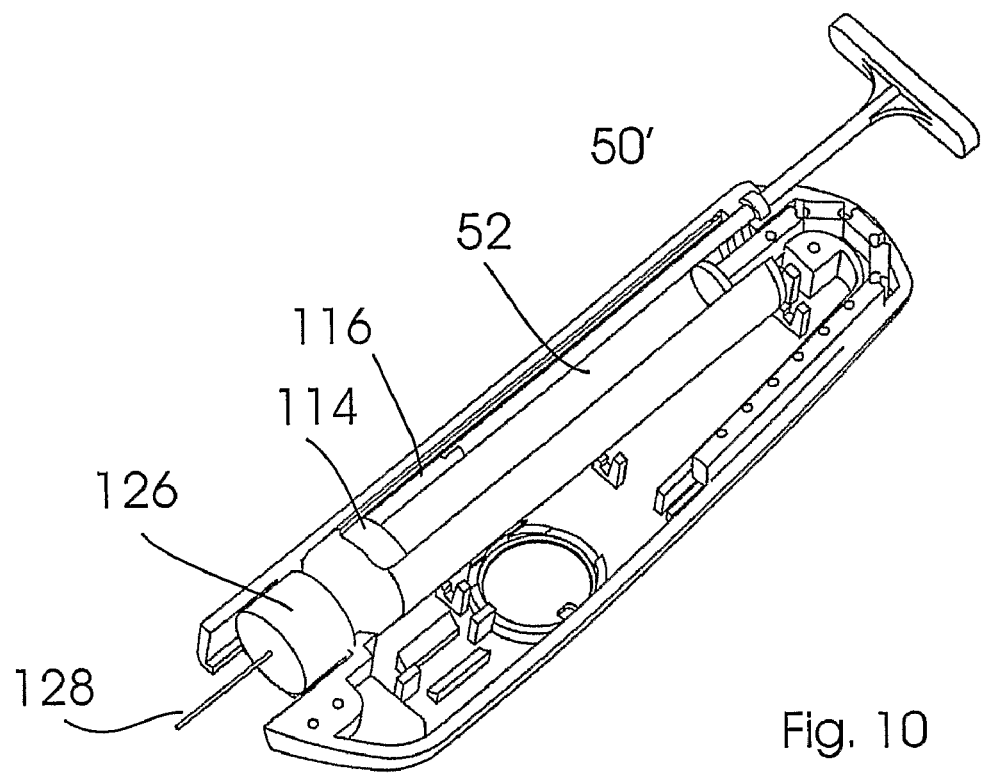
Figure 11:
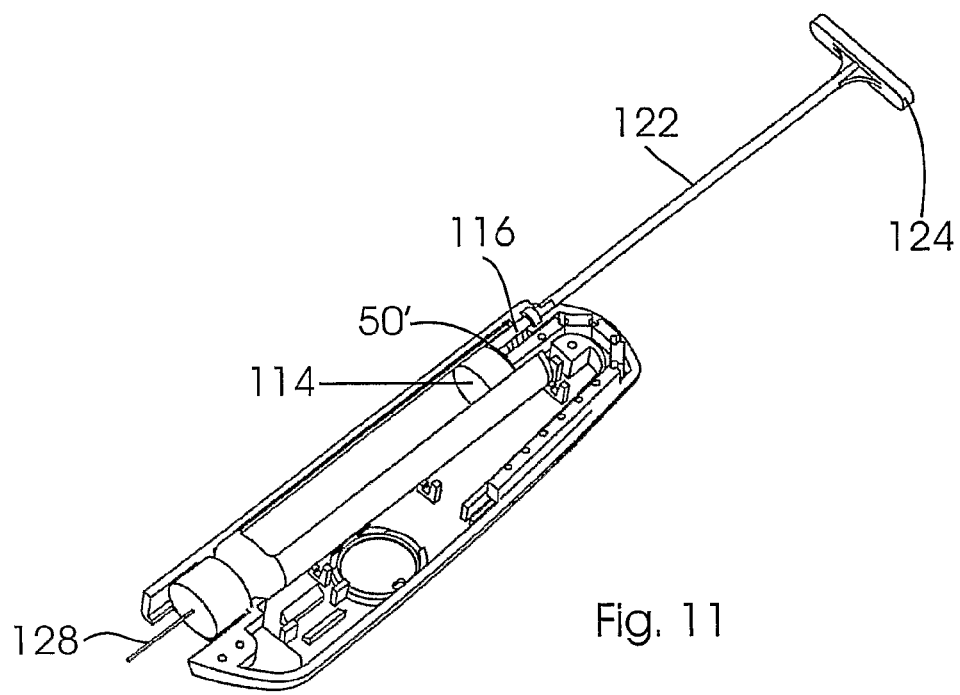

FIG. 10 illustrates the empty carpule 52 having the adapter 126 mounted on the protruding part 54 with the needle 128 extending into the interior of the carpule. After inserting the needle 128 into the not shown container containing the medication, the user pulls the handle 124 into the position illustrated in FIG. 11 hereby sucking the medicine from the container into the carpule. In this position the plunger 114 is brought into contact with the plunger 50' and provided that the external container with the medication has been connected correctly to the adapter 126, the carpule 52 is now filled with the medication.

Figure 12:
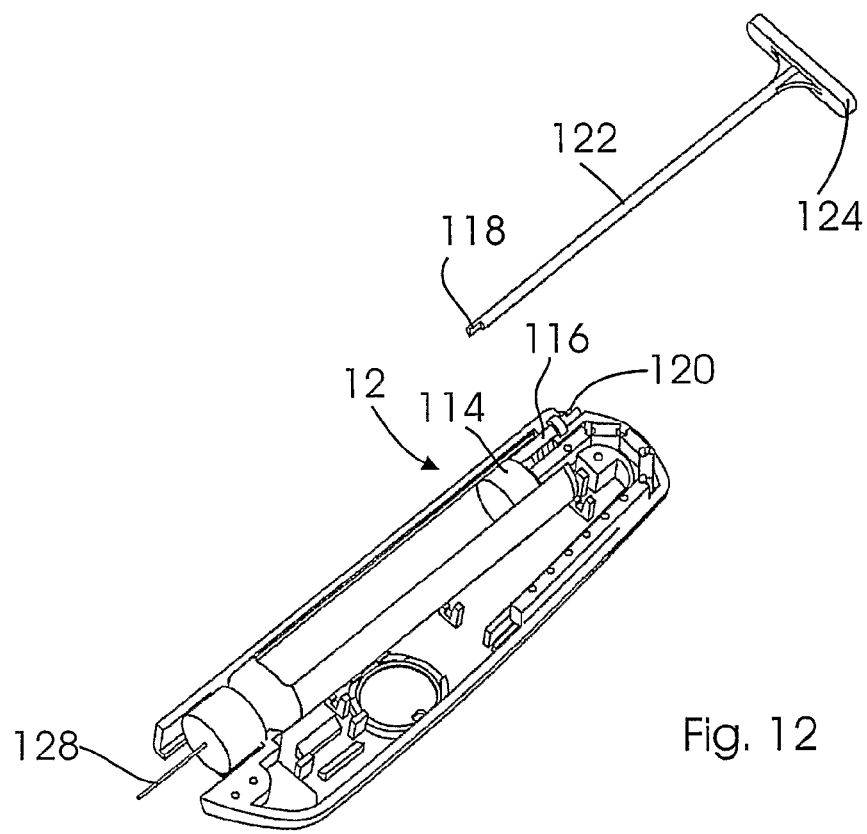
Figure 13:
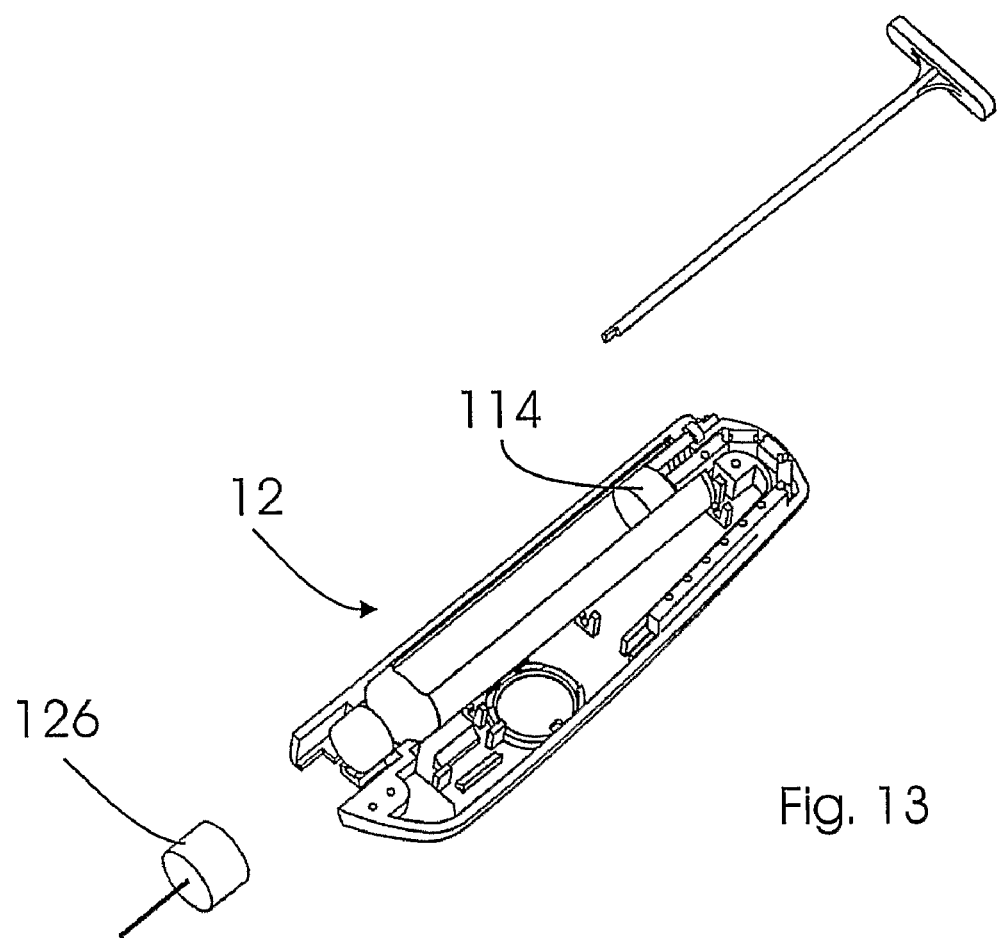

The rod 122 may now be separated from the rod 116 since the presence of the rod 122 and the handle 124 will be unpleasant to the wearer of the device. After the user retracts the rod 122, the user may break the rod 122 loose from the rod 116 as illustrated in FIG. 12. Next, the user removes the adapter 126 and the housing 12 is ready to be connected with the top part 92 and bottom part 94 as discussed above.

When the plunger head 114 is retracted, over pressure will be created in the interior of the housing 12 if not venting to the exterior is allowed. This may result in uncontrolled displacement of the plunger head and consequent uncontrolled dispensing of medicine.

The venting may take place by providing a not shown venting aperture in the housing. A non-return valve may be arranged in the venting aperture to avoid water entering the housing when the user bathes. The venting aperture may be covered by a hydro-phobic breathable membrane allowing air to exit but not water to enter.

The venting may also take place by providing the rod 122 with a longitudinally extending air venting channel.

The rods 122 and 166 may be substituted by a thread that is cut by a knife or scissors when the plunger head 114 has been fully retracted. Hereby the aperture through the sealing plug 126 will be so narrow that the resiliency of the silicone will close the aperture when the thread portion attached to the plunger head 114 is pulled out of the aperture when the plunger head 114 is displaced towards the projection 54. In the case of a rod 116, a not shown resilient flap is attached to the plug 126 so as to function as closure once the rod 116 had been pulled out of the aperture in the plug.

FIG. 14 is an enlarged view of the engagement parts 118 and 120 which are constituted by a projection 120 received in a not shown corresponding recess 118.

The handle 124 and rod 116, 122 are made from a non-toxic plastic material that may be readily disposed of.

The rod 122 may also be releasably connected directly to the plunger head 114 for instance by means of a screw thread or a bayonet engagement.

Figure 15:
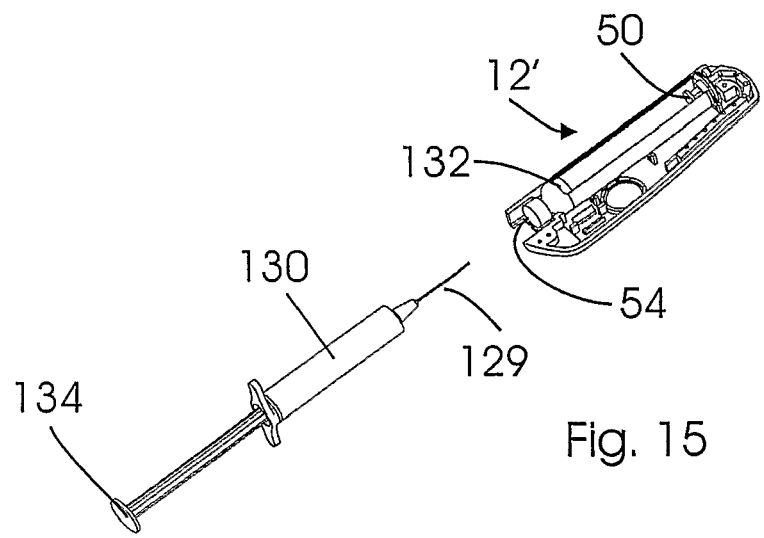
Figure 16:
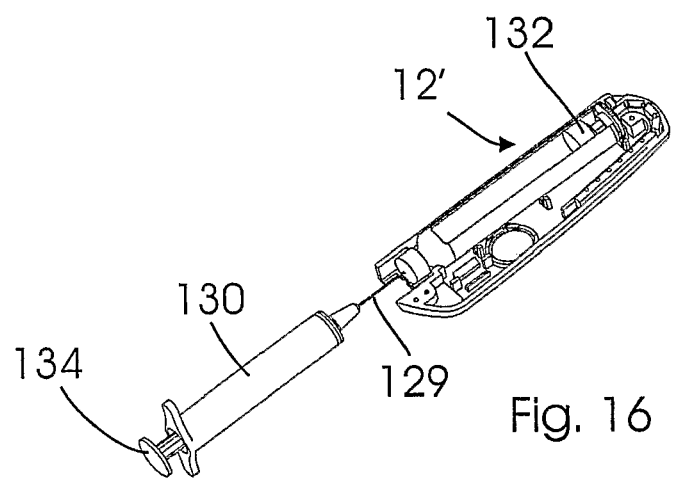
Figure 17:
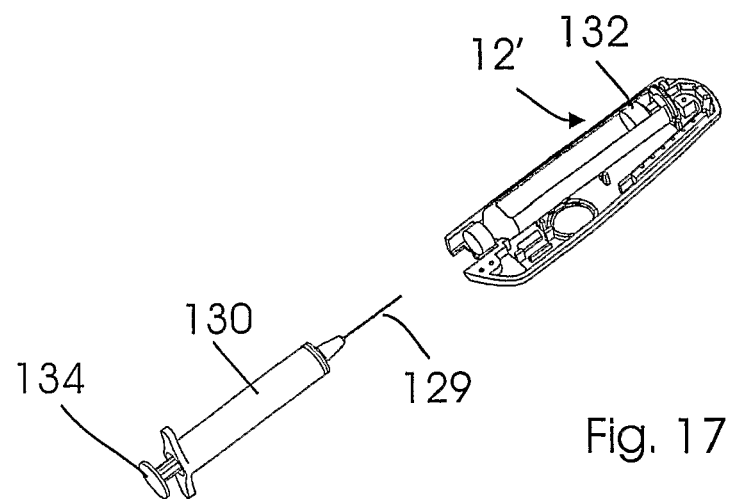

FIGS. 15-17 illustrates a method of filling the carpule 52 with medication using a syringe 130. The user is supplied with a housing 12' similar to that of FIG. 1 except that the carpule is empty and a plug or disc 132 is located at the end of the carpule, near the protruding part. The user inserts a needle 129 of a syringe 130 into the protruding part 54 and depresses a plunger 134 of the syringe 130.

FIG. 16 illustrates the situation wherein the user has fully depressed the plunger 134 and the plug 132 has been moved to the opposite end of the carpule as the interior of the carpule is now filled with medication. The user then retracts the syringe 130 from the dispensing protection 54 and disposes of the syringe 130 in a safe manner.

Also in this embodiment, venting of air must be possible to avoid build-up of pressure inside the housing 12'. A not shown venting aperture with a non-return valve or a gas permeable, water impermeable membrane may be provided.

FIG. 18 illustrates an alternative method of driving the toothed wheel 40 by means of a small electric step motor 134 driving a gear 136 engaging the toothed wheel 40.

Possible alternative embodiments of the driving mechanism driving the toothed wheel 40 or directly driving the threaded flexible piston rod 44 includes a coil spring exerting a pivoting force on the wheel 40. However, such an embodiment is not recommendable because of the possibility of malfunction with resulting sudden release of the energy stored in the spring and the consequent release of the entire or remaining content of medicine resulting in an overdose of medication.

FIGS. 19-23 illustrate a further alternative embodiment of an adapter 138 enabling the user to safely fill the carpule 52.

The adapter 138 receives a needle 140 of a syringe 142. The syringe 142 includes a plunger 146. The adapter 138 is provided with a not shown internal guide for the needle such that the needle is positioned precisely relative to the adapter. The guide is provided with a one-way lock allowing the needle to pass in one direction but preventing the needle from being pulled back in the opposite direction so that the needle may not be retracted from the adapter 138. Preferably, the needle 140 does not extend beyond the adapter 138 so that the syringe 142 including the needle 140 and the adapter 138 may ultimately be safely disposed of.

Figure 21:
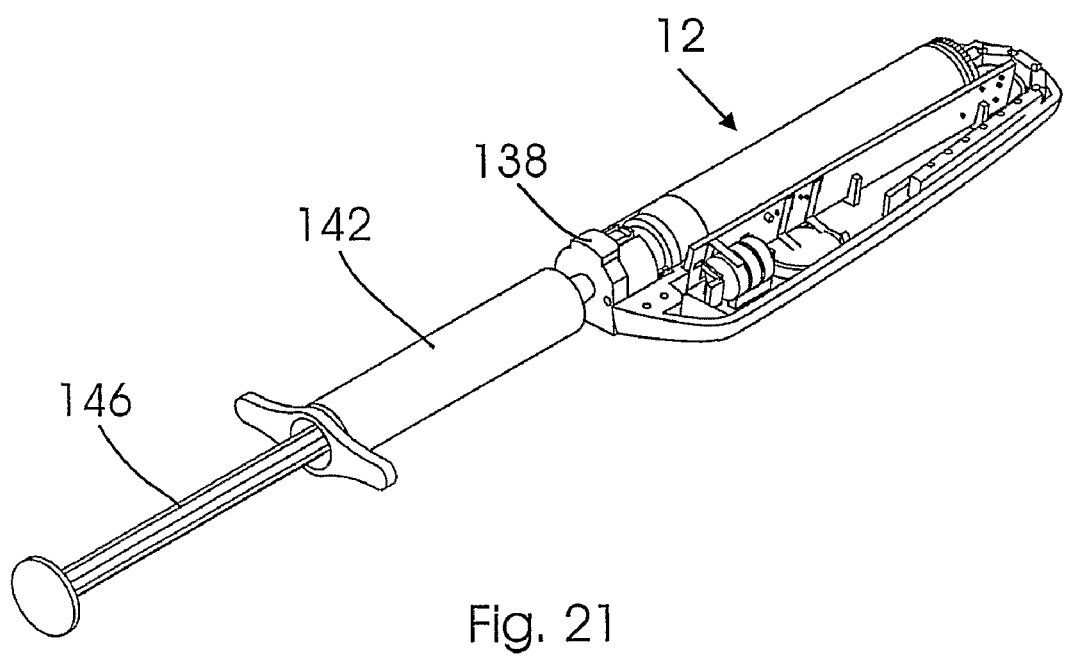
Figure 22:
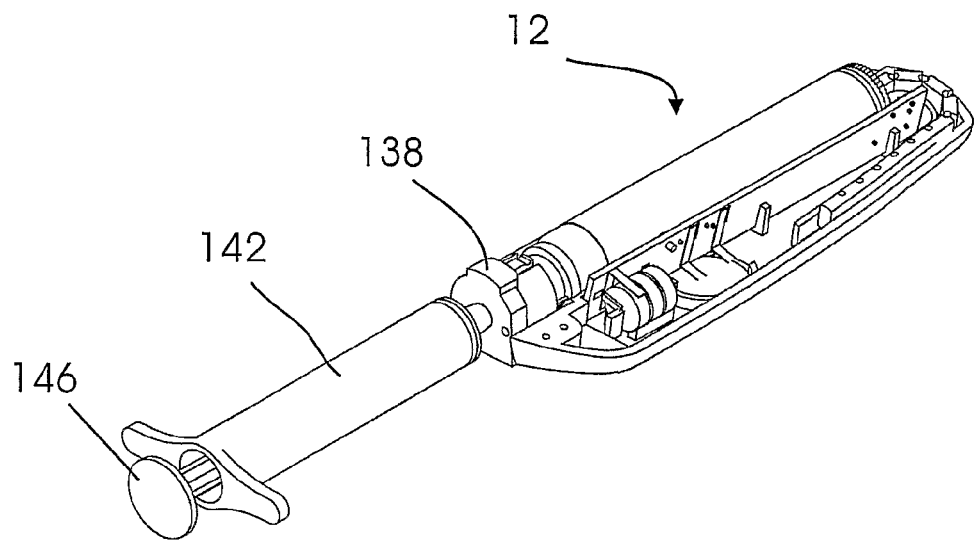
Figure 23:
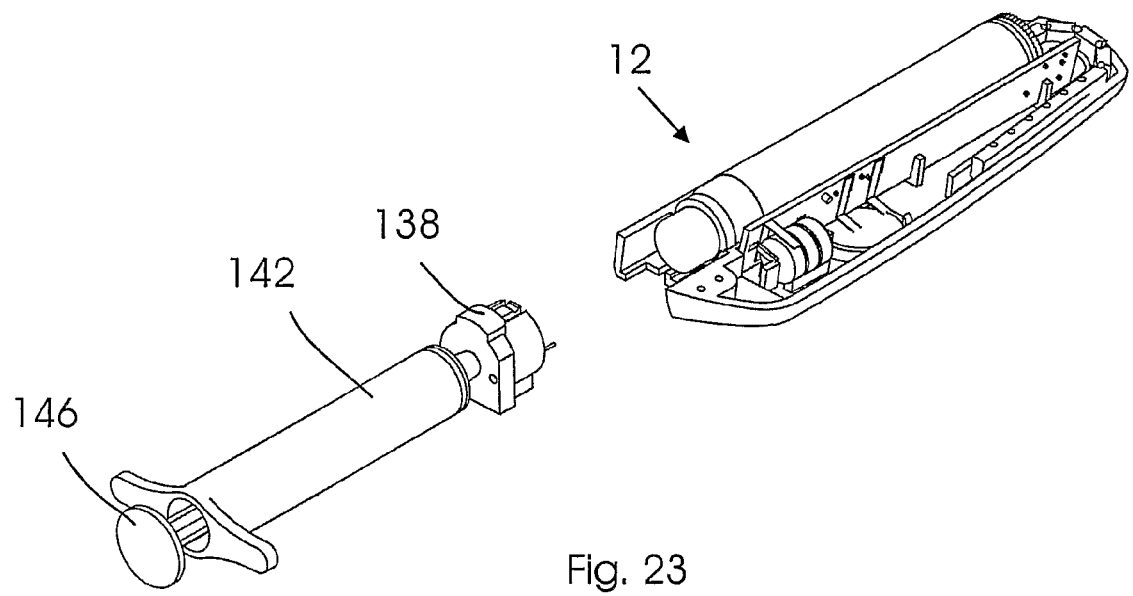

A second venting needle 144 for venting air in the housing 12 during filling of the carpule is located in the adapter in such a position that when the adapter is connected to the housing 12 as shown in FIG. 21, the venting needle perforates the sealing ring 56 and extends into the interior of the housing 12 thereby enabling release of excess pressure built up inside the housing 12 caused by the reduced volume when filling the carpule 52.

Ribs 138a provided on the adapter 138 fit snugly into corresponding not shown grooves in the housing 36 such that the angular position of the adapter 138 relative to the housing 12 is predetermined so that the perforation of the sealing ring 56 by the venting needle takes place at the predetermined location.

FIGS. 20-23 illustrate the steps of connecting the adapter 138 to the housing 12 and subsequently, filling the carpule with the medication stored in the syringe 142. The adapter 138 and the housing 12 may be dimensioned such that none of the needles 140 and 144 protrude outside the adapter 138.

The syringe may be supplied to the user already connected to the adapter or the syringe may be integral with the adapter.

The adapter and/or syringe may be provided with unique engagement means corresponding to unique engagement means on the housing 12 that only allow such a unique combination of adapter and syringe to be coupled to the housing such that only authorized medicine may be filled into the carpule.

Although the preferred actuating means for displacing the piston rod 44 is the SMA actuator described above, other actuating means may be employed.

FIG. 24 illustrates the back surface of the printed circuit board 58, whereon a solenoid 148 is located connected to a wire or thread 186 that in turn extends through an aperture 150 in the board and is fastened to the plate 78 such that a tension force applied to the thread by the solenoid results in pivoting of the plate 78 and flexing of the rod spring 66.

Referring now to FIGS. 25-27, a further alternative actuator for the toothed wheel 40 Comprises an actuator 149 that can rotate a pin 78a received in plate 78 to and fro so that the plate 78 is rotated to and fro between stops 85a and 85b as illustrated in FIGS. 25-27.

The actuator 149 may comprise an SMA thread arranged to pivot the pin 78a against the action of a spring or it may comprise a pivoting solenoid.

Referring now to FIGS. 28-29, it is illustrated therein that the dispensing device housing 34, 36 may be supplied without a carpule inserted therein such that the housing 34, 36 with internal pumping and other means may be supplied for use with carpules supplied from other sources and at different times than the supply of the housing such that different medicine from different suppliers may be dispensed by the device according to the invention.

Figure 19:
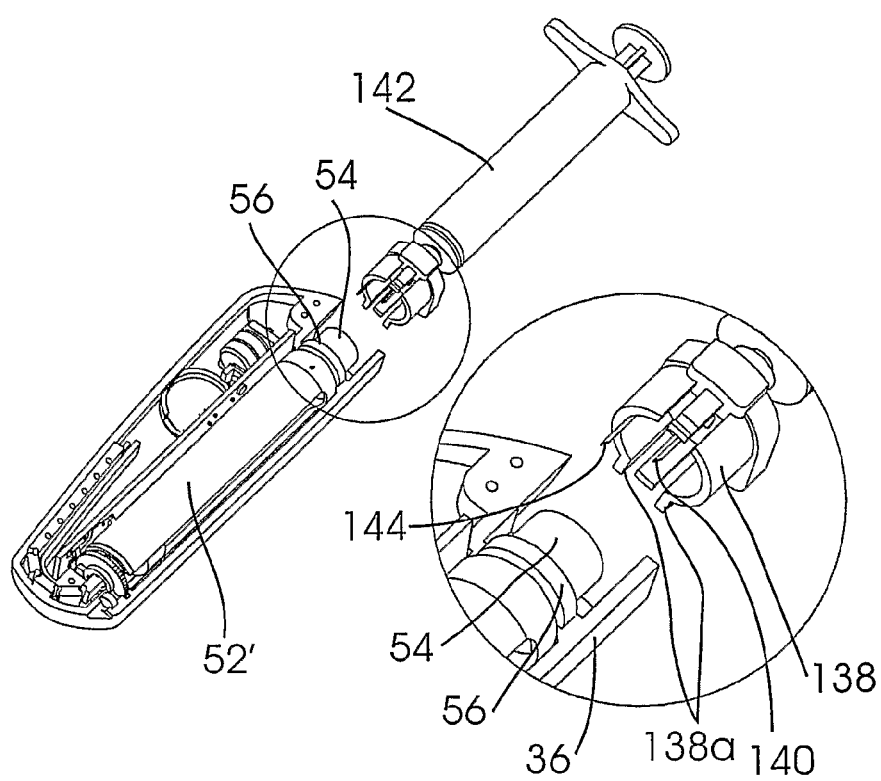
Figure 20:
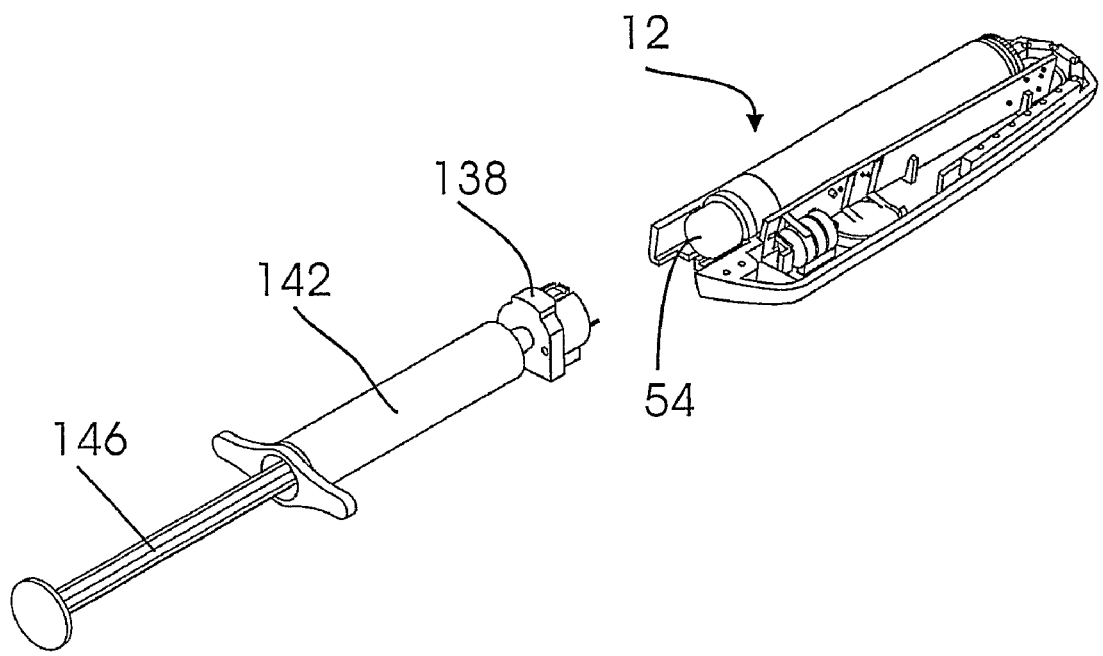

In the embodiment shown in FIG. 28, the carpule is a standard carpule 52 supplied by a great number of medicine suppliers. A sealing ring 56' corresponding to the sealing ring 56 of the embodiment shown in FIGS. 2 and 19 is attached to the upper and lower portions 92 and 94 of the catheter device 16 such that when the carpule 52 is inserted in the housing 34, 36 and the housing is connected to the catheter device, the sealing ring 56' will ensure that the interior of the housing is hermetically sealed.

The user may acquire the combination of the housing 34,36 and the catheter device or stylus 16 from one supplier and combine this combination with a carpule acquired from another supplier. This affords the user great flexibility and the supplier of the combination the possibility of reducing the price of the combination because of the greater production volume resulting from this flexibility. Furthermore, at the shelf life of the combination is much longer than the shelf life of the medicine in the carpule, a user may acquire a number of combinations and keep them in stock while acquiring the carpules with greater frequency.

In the embodiment shown in FIG. 29, a specialized carpule 52' with a permanently attached sealing collar 56" is inserted in the housing 34, 36 and the collar 56" is received in a not shown corresponding recess in the socket 92, 94 of the catheter device 16 such that the interior of the housing is hermetically sealed when the housing, carpule and catheter device are interconnected.

Hereby, the housing 34, 36 and the stylus assembly 16 can only be used in conjunction with a specific specialized carpule such that a medicine supplier ensures that the dispensing device with a pre-programmed function only may be used for dispensing a specific medicine.

The embodiments shown in FIGS. 28-29 may comprise any of the features of the embodiments shown in FIGS. 1-7g and 24-27. Furthermore, the means for displacing the piston inside the carpule 52 or 52' may be of any known type.

The means for specializing the carpule 56' so as only to correspond to a specific combination of housing 34, 36 and catheter or stylus assembly 16 may comprise any suitable special geometric features on the carpule corresponding to matching geometrical features of the housing and/or the stylus assembly.

For instance, one or more longitudinal grooves may be provided in the surface of the carpule 52' corresponding to matching protuberances provided in the periphery of the opening in the housing 34, 36 allowing only carpules with said grooves to be inserted in the compartment inside the housing adapted for receiving the carpule.

A dispensing device or insulin pump according to the invention may function in several different manners depending on the design and programming of the various control elements of the circuit board:

1. Stand Alone Pump with Constant Flow:

The pump functions as a constant flow pump and may be designed for different flow rates, for instance 20 units/24 hours, 30 units/24 hours, etc. By depressing the button and holding it down, the pumping programme is initiated and by again pressing the button down and holding it, the pumping programme is terminated while a short duration pressure on the button activates a bolus additional dosage of insulin of a certain magnitude.

2. Stand Alone Pump with Varying Flow:

A timing device is incorporated in the print board so that a standard programme controls the flow dispensed by the pump during recurring 24 hour periods. The pre-programmed operating instructions may for example result in a lower dosage at night than during the day and an extra dosage at mealtimes.

3. Programmable Pump Type 1:

The pump is not provided with a predetermined programme, but is provided with a programmable unit in the print board and can be programmed by the user or a doctor by means of a controller. The programming must be able to take place through the packing material in which the dispensing device is supplied so that the user can transport the device in a sterilised packaging on vacations or the like without having to carry the controller along. The controller is a dedicated unit that for instance via a USB plug can be connected to a PC or it can be provided with cellular telephone capability for transmission of data or other wireless connection capability. The controller can thus be programmed by a doctor or a user and be used for programming of the functioning of all subsequently used disposable dispensing devices.

4. Programmable Pump Type 2:

This pump functions in the same manner as programmable pump type 1, but the controller is a palm pilot or a laptop PC. This gives the additional advantage that the user may input health information and glucose level measurement results directly into the controller or programming unit and thus communicate such information to the doctor who may use this information when deciding whether the programming function of the controller or the programming unit is to be altered for subsequently used disposable dispensing devices.

5. Programmable Pump with Audio Input and Output:

By providing the dispensing device with a microphone/loudspeaker and a suitable recording/play-back chip in the printed circuit, short messages may be recorded by the dispensing device, and the short messages may be emitted by the device upon suitable manipulation of recording button mounted on the housing.

By means of this audio capability the user may record verbally formulated information regarding glucose levels, meal composition, exercise, etc. A timer may record the timing of each recorded message. A doctor may then use these recorded messages together with information about number and timing of bolus dosages, pumping stops and the programme utilised for the dispensing of the insulin so as to evaluate the treatment and decide upon any changes in the programming and instructions to the patient which may be recorded by the doctor via a mobile telephone or the like such that messages are automatically delivered to the user at predetermined times. Such a message could for example be 'remember to measure your glucose level' (message programme to be delivered by the dispensing device to the user each morning at 8 o'clock) and so on.

Furthermore, standard instructions can be included in the programming circuit so that the pump may deliver verbal messages to the user instead of audio signals such as beep sounds. The message could for instance be: 'Pump is stopped' or 'This is your third bolus in a row and you have taken a total of eight bolus dosages today' or 'The pump will be empty in two hours' and so on. Generally speaking, the audio capability described above will render the dispensing device provided with such capability much more user-friendly, especially for users initiating a treatment or not very disciplined as regards compliance.

6. Closed Loop Re-programmable Pump:

Either the controller or the computing unit mounted in the printed circuit may be programmed to react to information regarding actual glucose blood level inputted by the user perhaps together with other information, such as data regarding the timing and constitution of the last meal, to alter the programme of the dispensing flow or dosage to take into consideration this information such that the dispensing device to a certain extent constitutes a closed loop, fuzzy logic, semi-automatic self re-programming insulin dispensing device.

The invention claimed is:

1. A disposable, wearable medicine dispensing device comprising
    a housing;
    means for attaching said housing to the skin of a user of said device,
    a medicine container disposed in the housing;
    a flexible piston rod having an outer thread pattern on at least a portion thereof, wherein the piston rod moves from a flexed configuration in the housing toward a forward longitudinal direction to force medicine from the medicine container;
    a ratchet wheel having an inner thread pattern on a central aperture to mate with the outer thread pattern of the flexible piston rod such that rotation of said ratchet wheel in a forward rotational direction displaces the flexible piston rod in the forward longitudinal direction;
    a pivotable body disposed in the housing and adjustable between a forward position and a reset position, wherein adjustment of the pivotable body from the reset position to the forward position causes the ratchet wheel to rotate in said forward rotational direction;
    a spring device to bias said pivotable body toward the forward position; and
    an actuation system to controllably adjust the pivotable body toward the reset position, the actuation system comprising:
        a thread member coupled to the pivotable body, and
        a battery powered actuator coupled to the thread member so as to apply a tension force to the thread and thereby adjust the pivotable body.

2. The dispensing device of claim 1, further comprising a pawl member disposed on a pivotable body.

3. The dispensing device of claim 1, wherein the flexible piston rod comprises rod segments hinged together, the outer thread pattern being on at least a portion of the rod segments.

4. The dispensing device of claim 3, wherein rod segments are connected by hinges that comprise integrally formed, bendable material.

5. The dispensing device of claim 4, wherein the bendable material comprises a material selected from the group consisting of Nylon or POM (polyoxymethylene).

6. The dispensing device of claim 3, wherein the outer thread pattern is a discontinuous thread pattern.

7. The dispensing device of claim 1, wherein the battery powered actuator is a solenoid.

8. The dispensing device of claim 7, wherein the solenoid actuates in a linear motion to apply the tension force to the thread member.

9. A disposable, wearable medicine dispensing device, comprising:
    a wearable pump housing;
    an adhesive layer coupled to the housing so as to affix said housing to skin of a user,
    a medicine container disposed in the housing; a flexible piston rod having an outer thread pattern on at least a portion thereof, wherein the piston rod moves from a flexed configuration in the housing toward a forward longitudinal direction relative to the medicine container to force medicine from the medicine container;
    a ratchet wheel having an inner thread pattern on a central aperture to mate with the outer thread pattern of the flexible piston rod such that rotation of said ratchet wheel in a forward rotational direction displaces the flexible piston rod in the forward longitudinal direction;
    a pivotable body disposed in the housing and pivotable between a forward position and a reset position, wherein adjustment of the pivotable body from the reset position to the forward position causes the ratchet wheel to rotate in said forward rotational direction;
    a spring device to bias said pivotable body toward the forward position; and
    an actuation system to controllably adjust the pivotable body toward the reset position, the actuation system comprising:
        a thread member coupled to the pivotable body, and
        a battery-powered mechanical actuator to move an end portion of the thread member so as to apply a tension force to the thread member and thereby adjust the pivotable body.

10. The device of claim 9, wherein the wearable pump housing is wearable on a user's body and dispenses insulin to the user via a catheter tube while a handheld controller device having a user-interface buttons and a display communicates with the disposable dispensing device.

11. The device of claim 10, wherein the handheld controller device is connectable to a computer for transmission of data.

12. The device of claim 10, wherein the handheld controller device receives user input indicative of glucose level measurement results.

13. The device of claim 12, wherein the disposable dispensing device dispenses insulin to the user at a new dosage rate in response to the user input indicative of glucose level measurement results.

14. The dispensing device of claim 9, wherein the flexible piston rod comprises rod segments hinged together, the outer thread pattern being on at least a portion of the rod segments.

15. The dispensing device of claim 14, wherein the outer thread pattern is a discontinuous thread pattern.

16. The dispensing device of claim 9, wherein the battery-powered mechanical actuator is a solenoid.

17. A disposable, wearable medicine dispensing device, comprising:
- a wearable pump housing;
- a medicine container disposed in the housing;
- a flexible piston rod having an outer thread pattern on at least a portion thereof, wherein the piston rod moves from a flexed configuration in the housing toward a forward longitudinal direction relative to the medicine container to force medicine from the medicine container;
- a ratchet wheel having an inner thread pattern on a central aperture to mate with the outer thread pattern of the flexible piston rod such that rotation of said ratchet wheel in a forward rotational direction displaces the flexible piston rod in the forward longitudinal direction;
- a pivotable body disposed in the housing and pivotable between a forward position and a reset position, wherein adjustment of the pivotable body from the reset position to the forward position causes the ratchet wheel to rotate in said forward rotational direction;
- a spring device to bias said pivotable body toward the forward position; and
- an actuation system to controllably adjust the pivotable body toward the reset position, the actuation system comprising:
  - a thread member coupled to the pivotable body, and
  - a battery-powered mechanical actuator to move an end portion of the thread member so as to apply a tension force to the thread member and thereby adjust the pivotable body.

18. The device of claim 17, wherein the wearable pump housing is wearable on a user's body and dispenses insulin while a handheld controller device having a user-interface buttons and a display communicates with the disposable dispensing device.

19. The device of claim 18, wherein the handheld controller device receives user input indicative of glucose level measurement results.

20. The device of claim 19, wherein the disposable dispensing device dispenses insulin to the user at a new dosage rate in response to the user input indicative of glucose level measurement results.

* * * * *